US009480649B2

(12) United States Patent
Hansom et al.

(10) Patent No.: US 9,480,649 B2
(45) Date of Patent: Nov. 1, 2016

(54) LIPID MICROPARTICLE GROWTH FACTOR FORMULATIONS

(75) Inventors: Leah R. Hansom, Vadnais Heights, MN (US); William H. Frey, II, White Bear Lake, MN (US); John D. Hoekman, Seattle, WA (US); Jens Pohl, Hambrücken (DE)

(73) Assignees: Biopharm Gesellschaft zur biotechnologischen Entwicklung von Pharmaka mbH, Heidelberg (DE); HealthPartners Research Foundation, Minneapolis, MN (US)

(*) Notice: Subject to any disclaimer, the term of this patent is extended or adjusted under 35 U.S.C. 154(b) by 1905 days.

(21) Appl. No.: 12/446,884

(22) PCT Filed: Oct. 23, 2007

(86) PCT No.: PCT/EP2007/009198
§ 371 (c)(1),
(2), (4) Date: Jun. 15, 2009

(87) PCT Pub. No.: WO2008/049588
PCT Pub. Date: May 2, 2008

(65) Prior Publication Data
US 2010/0074959 A1    Mar. 25, 2010

(30) Foreign Application Priority Data

Oct. 23, 2006  (EP) .................... 06022159

(51) Int. Cl.
A61K 9/107 (2006.01)
A61K 38/47 (2006.01)
A61K 9/00 (2006.01)
A61K 38/18 (2006.01)

(52) U.S. Cl.
CPC ............ *A61K 9/1075* (2013.01); *A61K 38/18* (2013.01); *A61K 38/1841* (2013.01); *A61K 38/47* (2013.01); *A61K 9/0019* (2013.01); *A61K 9/0034* (2013.01); *A61K 9/0043* (2013.01)

(58) Field of Classification Search
None
See application file for complete search history.

(56) References Cited

U.S. PATENT DOCUMENTS

| 2001/0051595 | A1 | 12/2001 | Lyons et al. |
| 2002/0141971 | A1* | 10/2002 | Frey, II ................ 424/85.1 |
| 2004/0091459 | A1 | 5/2004 | Nimni |
| 2005/0049209 | A1* | 3/2005 | Chen ..................... 514/28 |

FOREIGN PATENT DOCUMENTS

| EP | 0 760 237 A1 | 3/1997 |
| EP | 1080720 A1 | 3/2001 |
| WO | 95 05078 A1 | 2/1995 |
| WO | 9904761 A1 | 2/1999 |
| WO | 0121154 A2 | 3/2001 |
| WO | 01 28520 A1 | 4/2001 |
| WO | 02/064166 A | 8/2002 |
| WO | 02/076494 A | 10/2002 |
| WO | 2006/094722 A | 9/2006 |

OTHER PUBLICATIONS

Seki et al., International Journal of Pharmaceutics, 2004; 273: 75-83.*
Uner, Pharmazie. May 2006; 61: 375-86.*
Fandel et al., J Sex Med, 2008; 5: 1866-1875.*
Hanson et al., Drug Delivery, 2012; 19: 149-154.*
Tenjarla et al., "Microemulsions: An Overview and Pharmaceutical Applications", Critical Reviews in Therapeutic Drug Carrier Systems, vol. 16, No. 5, Jan. 1999, pp. 461-520.
Benita et al., "Submicron Emulsions as Colloidal Drug Carriers for Intravenous Administration: Comprehensive Physicochemical Characterization", Journal of Pharmacetucial Sciences, vol. 82 Nov. 1993, No. 11, pp. 1069-1079.
Sullivan et al., "The role of growth/differentiation factor 5 (GDF5) in the induction and survival of midbrain . . . . ", Journal of Anatomy, vol. 207, No. 3, Sep. 2005, pp. 219-226.

* cited by examiner

*Primary Examiner* — Christina Borgeest
(74) *Attorney, Agent, or Firm* — Rothwell, Figg, Ernst & Manbeck, P.C.

(57) ABSTRACT

The present invention is directed to novel formulations and methods for the improved delivery and administration of hydrophobic therapeutic compounds that are substantially insoluble and/or susceptible to precipitation in aqueous solution at physiological pH, including, e.g., growth and differentiation factor-5 and related proteins. Many therapeutic compounds are hydrophobic at physiological pH levels.

66 Claims, 18 Drawing Sheets

```
  1 mrlpklltfl lwylawldle fictvlgapd lgqrpqgtrp glakaeaker pplarnvfrp
 61 gghsygggat nanarakggt gqtggltqpk kdepkklppr pggpepkpgh ppqtrqatar
121 tvtpkgqlpg gkappkagsv pssfllkkar epgpprepke pfrpppitph eymlslyrtl
181 sdadrkggns svkleaglan titsfidkgq ddrgpvvrkq ryvfdisale kdgllgaelr
241 ilrkkpsdta kpaapgggra aqlklsscps grqpaslldv rsvpgldgsg wevfdiwklf
301 rnfknsaqlc leleawergr avdlrglgfd raarqvheka lflvfgrtkk rdlffneika
361 rsgqddktvy eylfsqrrkr raplatrqgk rpsknlkarc srkalhvnfk dmgwddwiia
421 pleyeafhce glcefplrsh leptnhaviq tlmnsmdpes tpptccvptr lspisilfid
481 sannvvykqy edmvvescgc r
```

Fig. 1

```
hGDF-5 : CSRKALHVNFKDMGWDDWIIAPLEYEAFHCEGLCEFPLRSHLEPTNHAV
hGDF-6 : CSKKPLHVNFKELGWDDWIIAPLEYEAYHCEGVCDFPLRSHLEPTNHAI
hGDF-7 : CSRKPLHVDFKELGWDDWIIAPLDYEAYHCEGLCDFPLRSHLEPTNHAI hGDF-5 : IQTLMNSMDPESTPPTCCVPTRLSPISILFIDSANNVVYKQYEDMVVESCGCR
hGDF-6 : IQTLMNSMDPGSTPPSCCVPTKLTPISILYIDAGNNVVYKQYEDMVVESCGCR
hGDF-7 : IQTLLNSMAPDAAPASCCVPARLSPISILYIDAANNVVYKQYEDMVVEACGCR
```

Fig. 2

| Sequence | % Identity | Identical Residues |
|---|---|---|
| GDF-5 Homo | 100 | 102/102 |
| GDF-5 Mus | 99 | 101/102 |
| GDF-6 Mus | 86 | 88/102 |
| GDF-6 Homo | 85 | 87/102 |
| GDF-7 Homo | 81 | 83/102 |
| GDF-7 Mus | 80 | 82/102 |
| BMP-2A | 57 | 58/102 |
| BMP-2B | 57 | 58/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/103 |

Fig. 3

| Tissues | GDF5 Formulations ||||||||
|---|---|---|---|---|---|---|---|---|
| | 20 mM NaAc 7.0 avg nmol delivered ||| 200 mM NaAc 5.24 avg nmol delivered ||| LMP 3.61 avg nmol delivered- |||
| | Avg | SE | n | Avg | SE | n | Avg | SE | n |
| Blood Sample 1 (5:00) | 0,60 | 0,29 | 4 | 0,42 | 0,29 | 5 | - | - | - |
| Blood Sample 2 (10:00) | 0,68 | 0,09 | 4 | 0,62 | 0,09 | 4 | - | - | - |
| Blood Sample 3 (15:00) | 0,77 | 0,19 | 4 | 1,13 | 0,19 | 3 | - | - | - |
| Blood Sample 4 (20:00) | 1,21 | 0,20 | 3 | 1,54 | 0,20 | 2 | - | - | - |
| Blood Sample 5 (25:00) | 1,27 | 0,18 | 2 | 1,58 | 0,55 | 2 | 1,80 | 0,10 | 6 |
| Olfactory Epithelium | 1.582,31 | 455,14 | 4 | 1.571,21 | 455,14 | 5 | 61,84 | 20,81 | 6 |
| Olfactory Bulbs | 0,51 | 0,19 | 4 | 2,19 | 0,19 | 3 | 0,59 | 0,11 | 7 |
| Anterior Olfactory Nucleus | 0,21 | 0,11 | 4 | 0,41 | 0,11 | 5 | 0,27 | 0,05 | 6 |
| Trigeminal Nerve | 1,27 | 0,36 | 4 | 3,39 | 0,36 | 5 | 3,45 | 0,61 | 6 |
| Frontal Cortex | 0,08 | 0,01 | 3 | 0,71 | 0,01 | 5 | 0,18 | 0,04 | 6 |
| Caudate/Putamen | 0,11 | 0,02 | 4 | 0,23 | 0,02 | 5 | 0,17 | 0,04 | 7 |
| Septal Nucleus | 0,26 | 0,07 | 3 | 0,64 | 0,07 | 5 | 0,51 | 0,16 | 7 |
| Parietal Cortex | 0,14 | 0,03 | 3 | 0,79 | 0,03 | 5 | 0,22 | 0,04 | 6 |
| Temporal Cortex | 0,13 | 0,04 | 3 | 0,28 | 0,04 | 5 | - | - | - |
| Hippocampus | 0,06 | 0,01 | 4 | 0,24 | 0,01 | 5 | 0,15 | 0,03 | 5 |
| Thalamus | 0,05 | 0,01 | 4 | 0,16 | 0,01 | 5 | 0,14 | 0,03 | 6 |
| Hypothalamus | 0,10 | 0,02 | 4 | 0,25 | 0,02 | 5 | 0,47 | 0,10 | 7 |
| Midbrain | 0,06 | 0,01 | 4 | 0,25 | 0,01 | 5 | 0,26 | 0,04 | 7 |
| Pons | 0,06 | 0,01 | 4 | 0,18 | 0,01 | 5 | 0,47 | 0,09 | 7 |
| Medulla | 0,06 | 0,01 | 4 | 0,19 | 0,01 | 5 | 0,49 | 0,10 | 7 |
| Cerebellum | 0,06 | 0,01 | 4 | 0,12 | 0,01 | 5 | 0,30 | 0,05 | 7 |
| Upper Cervical Spinal Cord | 0,11 | 0,03 | 4 | 0,28 | 0,03 | 5 | 1,67 | 0,56 | 7 |
| Lower Cervical Spinal Cord | 0,07 | 0,02 | 4 | 0,18 | 0,02 | 5 | 0,07 | 0,01 | 7 |
| Thoracic Spinal Cord | 0,04 | 0,01 | 4 | 0,05 | 0,01 | 5 | 0,04 | 0,00 | 6 |
| Lumbar Spinal Cord | 0,07 | 0,01 | 4 | 0,05 | 0,01 | 5 | 0,05 | 0,01 | 7 |
| Superficial Nodes (4) | 0,37 | 0,06 | 4 | 0,36 | 0,06 | 5 | 0,59 | 0,11 | 6 |
| Cervical Nodes (2) | 1,51 | 0,30 | 4 | 1,37 | 0,30 | 5 | 3,50 | 0,97 | 7 |
| Axillary Nodes (2) | 0,51 | 0,04 | 4 | 2,79 | 0,04 | 5 | 0,27 | 0,03 | 6 |
| Spinal Dura | 0,65 | 0,38 | 4 | 0,71 | 0,38 | 5 | 0,23 | 0,04 | 6 |
| Dorsal Dura | 3,13 | 1,43 | 4 | 3,40 | 1,43 | 4 | 2,81 | 0,69 | 6 |
| Ventral Dura | 1,37 | 0,27 | 3 | 4,86 | 0,27 | 5 | 3,10 | 0,33 | 5 |
| Muscle | 0,32 | 0,06 | 4 | 0,21 | 0,06 | 5 | 0,19 | 0,04 | 7 |
| Liver | 0,30 | 0,06 | 4 | 0,96 | 0,06 | 5 | 0,36 | 0,04 | 7 |
| Kidney | 0,40 | 0,11 | 4 | 0,73 | 0,11 | 5 | 1,30 | 0,12 | 7 |
| Lung | 0,38 | 0,05 | 4 | 0,68 | 0,05 | 5 | 0,80 | 0,17 | 7 |
| Spleen | 0,20 | 0,05 | 4 | 0,36 | 0,05 | 5 | 0,57 | 0,05 | 7 |
| Thyroid | 35,59 | 8,15 | 3 | 13,15 | 8,15 | 4 | 43,99 | 11,69 | 7 |
| Urine | 0,61 | 0,12 | 3 | 0,45 | 0,12 | 5 | 0,55 | 0,18 | 6 |

FIG. 11

|  | GDLMP1 | GDLMP2 | GDLMP4 | GDLMP5 | GDLMP6 | GDLMP7 | GDLMP8 | AVERAGE |
|---|---|---|---|---|---|---|---|---|
| uL delivered | 40,0 | 37,5 | 38,4 | 38,4 | 38,4 | 38,4 | 38,4 | 38,5 |
| uCi delivered | 42,9 | 41,5 | 40,5 | 40,0 | 39,6 | 38,2 | 37,8 | 40,1 |
| Mg delivered | 0,10 | 0,09 | 0,10 | 0,10 | 0,10 | 0,10 | 0,10 | 0,10 |
| nmol delivered | 3,7 | 3,5 | 3,6 | 3,6 | 3,6 | 3,6 | 3,6 | 3,6 |
| Drug Delivery Time (min) | 14 | 14 | 14 | 14 | 14 | 14 | 14 | 14 |
| Perfusion Start (min after onset) | 28 | 28 | 28 | 29 | 29 | 27 | 27 | 28 |
| Rat weight | 280 | 266 | 285 | 292 | 297 | 289 | 295 | 286 |

| Tissue-Description | GDLMP1 | GDLMP2 | GDLMP4 | GDLMP5 | GDLMP6 | GDLMP7 | GDLMP8 | AVERAGE | SE |
|---|---|---|---|---|---|---|---|---|---|
| Blood Sample (25:00) | 1,54 | 1,90 | X | 1,72 | 1,68 | 2,27 | 1,71 | 1,80 | 0,10 |
| Olfactory Epithelium | X | 32,24 | 10,61 | 106,64 | 10,71 | 128,64 | 82,21 | 61,84 | 20,81 |
| Olfactory Bulbs | 0,38 | 1,06 | 0,85 | 0,36 | 0,26 | 0,70 | 0,56 | 0,59 | 0,11 |
| Anterior Olfactory Nucleus | 0,18 | 0,34 | X | 0,22 | 0,18 | 0,22 | 0,49 | 0,27 | 0,05 |
| Trigeminal Nerve | 5,56 | X | 1,43 | 3,02 | 2,80 | 4,78 | 3,11 | 3,45 | 0,61 |
| Frontal Cortex | 0,10 | 0,24 | X | 0,20 | 0,08 | 0,11 | 0,34 | 0,18 | 0,04 |
| Caudate/Putamen | 0,07 | 0,19 | 0,31 | 0,08 | 0,08 | 0,13 | 0,33 | 0,17 | 0,04 |
| Septal Nucleus | 0,23 | 0,32 | 1,09 | 0,17 | 0,19 | 0,41 | 1,16 | 0,51 | 0,16 |
| Parietal Cortex | 0,12 | 0,18 | X | 0,17 | 0,24 | 0,20 | 0,43 | 0,22 | 0,04 |
| Hippocampus | 0,04 | 0,14 | X | 0,19 | 0,15 | 0,22 | X | 0,15 | 0,03 |
| Thalamus | 0,05 | 0,20 | X | 0,14 | 0,09 | 0,16 | 0,22 | 0,14 | 0,03 |
| Hypothalamus | 0,16 | 0,30 | 0,90 | 0,44 | 0,27 | 0,55 | 0,71 | 0,47 | 0,10 |
| Midbrain | 0,12 | 0,32 | 0,21 | 0,24 | 0,19 | 0,37 | 0,39 | 0,26 | 0,04 |
| Pons | 0,17 | 0,43 | 0,36 | 0,29 | 0,89 | 0,60 | 0,58 | 0,47 | 0,09 |
| Medulla | 0,16 | 0,68 | 0,21 | 0,40 | 0,40 | 0,78 | 0,78 | 0,49 | 0,10 |
| Cerebellum | 0,12 | 0,34 | 0,19 | 0,21 | 0,29 | 0,48 | 0,45 | 0,30 | 0,05 |
| Upper Cervical Spinal Cord | 2,65 | 0,54 | 3,76 | 0,65 | 0,16 | 0,71 | 3,20 | 1,67 | 0,56 |
| Lower Cervical Spinal Cord | 0,04 | 0,06 | 0,09 | 0,06 | 0,05 | 0,07 | 0,10 | 0,07 | 0,01 |
| Thoracic Spinal Cord | 0,05 | 0,05 | X | 0,04 | 0,04 | 0,04 | 0,04 | 0,04 | 0,00 |
| Lumbar Spinal Cord | 0,08 | 0,04 | 0,07 | 0,05 | 0,02 | 0,04 | 0,03 | 0,05 | 0,01 |
| Superficial Nodes (4) | 0,31 | X | 0,90 | 0,66 | 0,75 | 0,22 | 0,71 | 0,59 | 0,11 |
| Cervical Nodes (2) | 1,29 | 8,32 | 3,01 | 1,54 | 2,24 | 2,49 | 5,60 | 3,50 | 0,97 |
| Axillary Nodes (2) | 0,21 | 0,23 | X | 0,39 | 0,23 | 0,26 | 0,27 | 0,27 | 0,03 |
| Spinal Dura | X | 0,19 | 0,39 | 0,17 | 0,17 | 0,20 | 0,27 | 0,23 | 0,04 |
| Dorsal Dura | 4,31 | X | 1,90 | 2,49 | 1,52 | 1,20 | 5,45 | 2,81 | 0,69 |
| Ventral Dura | X | X | 3,76 | 3,40 | 1,97 | 2,78 | 3,61 | 3,10 | 0,33 |
| Muscle | 0,11 | 0,19 | 0,23 | 0,16 | 0,08 | 0,18 | 0,376 | 0,19 | 0,04 |
| Liver | 0,37 | 0,38 | 0,52 | 0,23 | 0,18 | 0,35 | 0,47 | 0,36 | 0,04 |
| Kidney | 1,28 | 0,89 | 1,55 | 1,19 | 1,34 | 1,05 | 1,80 | 1,30 | 0,12 |
| Lung | 0,43 | 0,39 | 1,37 | 0,55 | 0,81 | 1,51 | 0,52 | 0,80 | 0,17 |
| Spleen | 0,45 | 0,65 | 0,68 | 0,66 | 0,68 | 0,42 | 0,44 | 0,57 | 0,05 |
| Thyroid | 13,81 | 79,67 | 33,84 | 93,93 | 15,79 | 32,14 | 38,74 | 43,99 | 11,69 |
| Urine | 0,05 | 0,65 | X | 0,67 | 0,11 | 1,23 | 0,61 | 0,55 | 0,18 |

Notes: X = outlier removed

FIG.12

| Tissues | GDF5 Formulations | | |
|---|---|---|---|
| | Aqueous Solution 1 | Aqueous Solution 2 | LMP |
| | 20 mM NaAc pH 4.25 | 200 mM NaAc pH 4.0 | 20 mM Suc + 10 mM NaAc pH 7.0 |
| Blood Sample 1 (5:00) | 0,31 | 0,29 | - |
| Blood Sample 2 (10:00) | 0,35 | 0,43 | - |
| Blood Sample 3 (15:00) | 0,40 | 0,78 | - |
| Blood Sample 4 (20:00) | 0,63 | 1,06 | - |
| Blood Sample 5 (25:00) | 0,66 | 1,09 | 1,80 |
| Olfactory Epithelium | 816,02 | 1.082,45 | 61,84 |
| Olfactory Bulbs | 0,26 | 1,51 | 0,59 |
| Anterior Olfactory Nucleus | 0,11 | 0,28 | 0,27 |
| Trigeminal Nerve | 0,66 | 2,33 | 3,45 |
| Frontal Cortex | 0,04 | 0,49 | 0,18 |
| Caudate/Putamen | 0,06 | 0,16 | 0,17 |
| Septal Nucleus | 0,13 | 0,44 | 0,51 |
| Parietal Cortex | 0,07 | 0,54 | 0,22 |
| Temporal Cortex | 0,07 | 0,20 | - |
| Hippocampus | 0,03 | 0,16 | 0,15 |
| Thalamus | 0,03 | 0,11 | 0,14 |
| Hypothalamus | 0,05 | 0,17 | 0,47 |
| Midbrain | 0,03 | 0,17 | 0,26 |
| Pons | 0,03 | 0,12 | 0,47 |
| Medulla | 0,03 | 0,13 | 0,49 |
| Cerebellum | 0,03 | 0,08 | 0,30 |
| Upper Cervical Spinal Cord | 0,06 | 0,19 | 1,67 |
| Lower Cervical Spinal Cord | 0,04 | 0,13 | 0,07 |
| Thoracic Spinal Cord | 0,02 | 0,03 | 0,04 |
| Lumbar Spinal Cord | 0,03 | 0,03 | 0,05 |
| Superficial Nodes (4) | 0,19 | 0,25 | 0,59 |
| Cervical Nodes (2) | 0,78 | 0,94 | 3,50 |
| Axillary Nodes (2) | 0,26 | 1,92 | 0,27 |
| Spinal Dura | 0,33 | 0,49 | 0,23 |
| Dorsal Dura | 1,62 | 2,34 | 2,81 |
| Ventral Dura | 0,71 | 3,35 | 3,10 |
| Muscle | 0,16 | 0,15 | 0,19 |
| Liver | 0,15 | 0,66 | 0,36 |
| Kidney | 0,21 | 0,50 | 1,30 |
| Lung | 0,20 | 0,47 | 0,80 |
| Spleen | 0,10 | 0,25 | 0,57 |
| Thyroid | 18,36 | 9,06 | 43,99 |
| Urine | 0,31 | 0,31 | 0,55 |

FIG. 13

| Tissues | GDF5 Formulations | |
|---|---|---|
| | Aqueous Solution 1 | LMP |
| | 20 mM NaAc | 20 mM Suc + 10 mM NaAc |
| | pH 4.25 | pH 7.0 |
| Olfactory Epithelium | 1.244,17 | 34,30 |
| Olfactory Bulbs | 0,40 | 0,33 |
| Anterior Olfactory Nucleus | 0,16 | 0,15 |
| Trigeminal Nerve | 1,00 | 1,91 |
| Frontal Cortex | 0,06 | 0,10 |
| Caudate/Putamen | 0,09 | 0,09 |
| Septal Nucleus | 0,20 | 0,28 |
| Parietal Cortex | 0,11 | 0,12 |
| Temporal Cortex | 0,10 | |
| Hippocampus | 0,05 | 0,08 |
| Thalamus | 0,04 | 0,08 |
| Hypothalamus | 0,08 | 0,26 |
| Midbrain | 0,05 | 0,15 |
| Pons | 0,05 | 0,26 |
| Medulla | 0,05 | 0,27 |
| Cerebellum | 0,05 | 0,16 |
| Upper Cervical Spinal Cord | 0,09 | 0,92 |
| Lower Cervical Spinal Cord | 0,06 | 0,04 |
| Thoracic Spinal Cord | 0,03 | 0,02 |
| Lumbar Spinal Cord | 0,05 | 0,03 |

FIG. 14

| Tissues | GDF5 Formulations | |
|---|---|---|
| | Aqueous Solution 1 | LMP |
| | 20 mM NaAc | 20 mM Suc + 10 mM NaAc |
| | pH 4.25 | pH 7.0 |
| Blood Sample 5 (25:00) | 4,01 | 9,52 |
| Olfactory Epithelium | 4.986,09 | 326,45 |
| Olfactory Bulbs | 1,62 | 3,14 |
| Anterior Olfactory Nucleus | 0,66 | 1,43 |
| Trigeminal Nerve | 4,01 | 18,21 |
| Frontal Cortex | 0,26 | 0,94 |
| Caudate/Putamen | 0,35 | 0,90 |
| Septal Nucleus | 0,82 | 2,69 |
| Parietal Cortex | 0,44 | 1,18 |
| Temporal Cortex | 0,41 | |
| Hippocampus | 0,20 | 0,79 |
| Thalamus | 0,17 | 0,76 |
| Hypothalamus | 0,31 | 2,51 |
| Midbrain | 0,20 | 1,39 |
| Pons | 0,18 | 2,50 |
| Medulla | 0,20 | 2,58 |
| Cerebellum | 0,20 | 1,57 |
| Upper Cervical Spinal Cord | 0,34 | 8,80 |
| Lower Cervical Spinal Cord | 0,23 | 0,35 |
| Thoracic Spinal Cord | 0,14 | 0,23 |
| Lumbar Spinal Cord | 0,21 | 0,25 |

FIG. 15

| No. | Sham | Control | Vehicle | High (10μcg) | Middle (2μcg) | Low (0.4μcg) |
|---|---|---|---|---|---|---|
| # 1 | 121,20 | 18,09 | 25,10 | 9,65 | 103,10 | 77,28 |
| # 2 | 93,04 | 15,68 | 17,10 | 13,33 | 75,70 | 127,66 |
| # 3 | 176,22 | 26,44 | 28,00 | 53,80 | 82,60 | 96,02 |
| # 4 | 107,10 | 5,63 | 13,60 | 40,90 | 22,60 | 84,78 |
| # 5 | 121,30 | 20,70 | 10,30 | 18,10 | 119,10 | 132,93 |
| # 6 | 92,94 | 14,20 | 21,60 | 55,50 | 19,60 | 142,69 |
| # 7 | 93,56 | 8,70 | 28,26 | 19,40 | 62,60 | 59,91 |
| # 8 | 83,82 | 10,45 | 45,37 | 4,70 | 91,60 | 77,71 |
| | | | | | | |
| Mean | 111,15 | 14,99 | 23,67 | 26,92 | 72,11 | 99,87 |
| SD | 29,69 | 6,78 | 10,96 | 20,16 | 35,80 | 30,56 |

| Groups (n=5) | Mean ± SE no. nNOS-positive nerve fibers | Mean ± SE no. TUNEL-positive cells |
|---|---|---|
| Uninjured controls | 244 ± 25* | 12.3 ± 2.7* |
| Injured controls | 42 ± 9 | 35.7 ± 5.9 |
| 0.4 µg GDF-5 | 162 ± 49* | 5.3 ± 1.2* |
| 2 µg GDF-5 | 86 ± 14 | 25.1 ± 3.2* |
| 10 µg GDF-5 | 55 ± 19 | 57.7 ± 6.1* |

* $p < 0.05$ vs. injured controls

FIG. 18

SEQUENCE LISTING

```
<160> NUMBER OF SEQ ID NOS: 7

<210> SEQ ID NO 1
<211> LENGTH: 2703
<212> TYPE: DNA
<213> ORGANISM: homo sapiens
<220> FEATURE:
<221> NAME/KEY: CDS
<222> LOCATION: (640)..(2142)
<223> OTHER INFORMATION: GDF-5 precursor

<400> SEQUENCE: 1
```

-continued

```
ccatggcctc gaaagggcag cggtgatttt tttcacataa atatatcgca cttaaatgag    60
tttagacagc atgacatcag agagtaatta aattggtttg ggttggaatt ccgtttccaa   120
ttcctgagtt caggtttgta aaagattttt ctgagcacct gcaggcctgt gagtgtgtgt   180
gtgtgtgtgt gtgtgtgtgt gtgtgtgtga agtattttca ctggaaagga ttcaaaacta   240
gggggaaaaa aaaactggag cacacaggca gcattacgcc attcttcctt cttggaaaaa   300
tccctcagcc ttatacaagc ctccttcaag ccctcagtca gttgtgcagg agaaagggg    360 cggttggctt tctcctttca agaacgagtt attttcagct gctgactgga gacggtgcac   420
gtctggatac gagagcattt ccactatggg actggataca aacacacacc cggcagactt   480
caagagtctc agactgagga gaaagccttt ccttctgctg ctactgctgc tgccgctgct   540
tttgaaagtc cactcctttc atggttttc ctgccaaacc agaggcacct ttgctgctgc   600
cgctgttctc tttggtgtca ttcagcggct ggccagagg atg aga ctc ccc aaa      654
                                          Met Arg Leu Pro Lys
                                            1               5 ctc ctc act ttc ttg ctt tgg tac ctg gct tgg ctg gac ctg gaa ttc    702
Leu Leu Thr Phe Leu Leu Trp Tyr Leu Ala Trp Leu Asp Leu Glu Phe
         10                  15                  20 atc tgc act gtg ttg ggt gcc cct gac ttg ggc cag aga ccc cag ggg    750
Ile Cys Thr Val Leu Gly Ala Pro Asp Leu Gly Gln Arg Pro Gln Gly
     25                  30                  35 acc agg cca gga ttg gcc aaa gca gag gcc aag gag agg ccc ccc ctg    798
Thr Arg Pro Gly Leu Ala Lys Ala Glu Ala Lys Glu Arg Pro Pro Leu
 40                  45                  50 gcc cgg aac gtc ttc agg cca ggg ggt cac agc tat ggt ggg ggg gcc    846
Ala Arg Asn Val Phe Arg Pro Gly Gly His Ser Tyr Gly Gly Gly Ala
         55                  60                  65 acc aat gcc aat gcc agg gca aag gga ggc acc ggg cag aca gga ggc    894
Thr Asn Ala Asn Ala Arg Ala Lys Gly Gly Thr Gly Gln Thr Gly Gly
 70                  75                  80                  85 ctg aca cag ccc aag aag gat gaa ccc aaa aag ctg ccc ccc aga ccg    942
Leu Thr Gln Pro Lys Lys Asp Glu Pro Lys Lys Leu Pro Pro Arg Pro
             90                  95                 100 ggc ggc cct gaa ccc aag cca gga cac cct ccc caa aca agg cag gct    990
Gly Gly Pro Glu Pro Lys Pro Gly His Pro Pro Gln Thr Arg Gln Ala
        105                 110                 115 aca gcc cgg act gtg acc cca aaa gga cag ctt ccc gga ggc aag gca   1038
Thr Ala Arg Thr Val Thr Pro Lys Gly Gln Leu Pro Gly Gly Lys Ala
    120                 125                 130 ccc cca aaa gca gga tct gtc ccc agc tcc ttc ctg ctg aag aag gcc   1086
Pro Pro Lys Ala Gly Ser Val Pro Ser Ser Phe Leu Leu Lys Lys Ala
135                 140                 145 agg gag ccc ggg ccc cca cga gag ccc aag gag ccg ttt cgc cca ccc   1134
Arg Glu Pro Gly Pro Pro Arg Glu Pro Lys Glu Pro Phe Arg Pro Pro
150                 155                 160                 165 ccc atc aca ccc cac gag tac atg ctc tcg ctg tac agg acg ctg tcc   1182
Pro Ile Thr Pro His Glu Tyr Met Leu Ser Leu Tyr Arg Thr Leu Ser
                170                 175                 180 gat gct gac aga aag gga ggc aac agc agc gtg aag ttg gag gct ggc   1230
Asp Ala Asp Arg Lys Gly Gly Asn Ser Ser Val Lys Leu Glu Ala Gly
            185                 190                 195 ctg gcc aac acc atc acc agc ttt att gac aaa ggg caa gat gac cga   1278
Leu Ala Asn Thr Ile Thr Ser Phe Ile Asp Lys Gly Gln Asp Asp Arg
        200                 205                 210 ggt ccc gtg gtc agg aag cag agg tac gtg ttt gac att agt gcc ctg   1326
Gly Pro Val Val Arg Lys Gln Arg Tyr Val Phe Asp Ile Ser Ala Leu
    215                 220                 225
```

-continued

```
gag aag gat ggg ctg ctg ggg gcc gag ctg cgg atc ttg cgg aag aag    1374
Glu Lys Asp Gly Leu Leu Gly Ala Glu Leu Arg Ile Leu Arg Lys Lys
230                 235                 240                 245 ccc tcg gac acg gcc aag cca gcg gcc ccc gga ggc ggg cgg gct gcc    1422
Pro Ser Asp Thr Ala Lys Pro Ala Ala Pro Gly Gly Gly Arg Ala Ala
                250                 255                 260 cag ctg aag ctg tcc agc tgc ccc agc ggc cgg cag ccg gcc tcc ttg    1470
Gln Leu Lys Leu Ser Ser Cys Pro Ser Gly Arg Gln Pro Ala Ser Leu
            265                 270                 275 ctg gat gtg cgc tcc gtg cca ggc ctg gac gga tct ggc tgg gag gtg    1518
Leu Asp Val Arg Ser Val Pro Gly Leu Asp Gly Ser Gly Trp Glu Val
        280                 285                 290 ttc gac atc tgg aag ctc ttc cga aac ttt aag aac tcg gcc cag ctg    1566
Phe Asp Ile Trp Lys Leu Phe Arg Asn Phe Lys Asn Ser Ala Gln Leu
    295                 300                 305 tgc ctg gag ctg gag gcc tgg gaa cgg ggc agg gcc gtg gac ctc cgt    1614
Cys Leu Glu Leu Glu Ala Trp Glu Arg Gly Arg Ala Val Asp Leu Arg
310                 315                 320                 325 ggc ctg ggc ttc gac cgc gcc gcc cgg cag gtc cac gag aag gcc ctg    1662
Gly Leu Gly Phe Asp Arg Ala Ala Arg Gln Val His Glu Lys Ala Leu
                330                 335                 340 ttc ctg gtg ttt ggc cgc acc aag aaa cgg gac ctg ttc ttt aat gag    1710
Phe Leu Val Phe Gly Arg Thr Lys Lys Arg Asp Leu Phe Phe Asn Glu
            345                 350                 355 att aag gcc cgc tct ggc cag gac gat aag acc gtg tat gag tac ctg    1758
Ile Lys Ala Arg Ser Gly Gln Asp Asp Lys Thr Val Tyr Glu Tyr Leu
        360                 365                 370 ttc agc cag cgg cga aaa cgg cgg gcc cca ctg gcc act cgc cag ggc    1806
Phe Ser Gln Arg Arg Lys Arg Arg Ala Pro Leu Ala Thr Arg Gln Gly
    375                 380                 385 aag cga ccc agc aag aac ctt aag gct cgc tgc agt cgg aag gca ctg    1854
Lys Arg Pro Ser Lys Asn Leu Lys Ala Arg Cys Ser Arg Lys Ala Leu
390                 395                 400                 405 cat gtc aac ttc aag gac atg ggc tgg gac gac tgg atc atc gca ccc    1902
His Val Asn Phe Lys Asp Met Gly Trp Asp Asp Trp Ile Ile Ala Pro
                410                 415                 420 ctt gag tac gag gct ttc cac tgc gag ggg ctg tgc gag ttc cca ttg    1950
Leu Glu Tyr Glu Ala Phe His Cys Glu Gly Leu Cys Glu Phe Pro Leu
            425                 430                 435 cgc tcc cac ctg gag ccc acg aat cat gca gtc atc cag acc ctg atg    1998
Arg Ser His Leu Glu Pro Thr Asn His Ala Val Ile Gln Thr Leu Met
        440                 445                 450 aac tcc atg gac ccc gag tcc aca cca ccc acc tgc tgt gtg ccc acg    2046
Asn Ser Met Asp Pro Glu Ser Thr Pro Pro Thr Cys Cys Val Pro Thr
    455                 460                 465 cgg ctg agt ccc atc agc atc ctc ttc att gac tct gcc aac aac gtg    2094
Arg Leu Ser Pro Ile Ser Ile Leu Phe Ile Asp Ser Ala Asn Asn Val
470                 475                 480                 485 gtg tat aag cag tat gag gac atg gtc gtg gag tcg tgt ggc tgc agg    2142
Val Tyr Lys Gln Tyr Glu Asp Met Val Val Glu Ser Cys Gly Cys Arg
                490                 495                 500 tagcagcact ggccctctgt cttcctgggt ggcacatccc aagagcccct tcctgcactc    2202
ctggaatcac agaggggtca ggaagctgtg gcaggagcat ctacacagct ggggtgaaag    2262
gggattccaa taagcttgct cgctctctga gtgtgacttg ggctaaaggc cccctttttat    2322 ccacaagttc ccctggctga ggattgctgc ccgtctgctg atgtgaccag tggcaggcac    2382
aggtccaggg agacagactc tgaatgggac tgagtcccag gaaacagtgc tttccgatga    2442
```

-continued

```
gactcagccc accatttctc ctcacctggg ccttctcagc ctctggactc tcctaagcac   2502
ctctcaggag agccacaggt gccactgcct cctcaaatca catttgtgcc tggtgacttc   2562
ctgtccctgg gacagttgag aagctgactg ggcaagagtg ggagagaaga ggagagggct   2622
tggatagagt tgaggagtgt gaggctgtta gactgttaga tttaaatgta tattgatgag   2682
ataaaaagca aaactgtgcc t                                             2703
```

<210> SEQ ID NO 2
<211> LENGTH: 501
<212> TYPE: PRT
<213> ORGANISM: homo sapiens

<400> SEQUENCE: 2

| Met | Arg | Leu | Pro | Lys | Leu | Leu | Thr | Phe | Leu | Leu | Trp | Tyr | Leu | Ala | Trp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val

```
                    325                 330                 335
His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 3
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: human mature monomeric GDF-5

<400> SEQUENCE: 3 gca cca cta gca act cgt cag ggc aag cga ccc agc aag aac ctt aag      48
Ala Pro Leu Ala Thr Arg Gln Gly Lys Arg Pro Ser Lys Asn Leu Lys
1               5                   10                  15 gct cgc tgc agt cgg aag gca ctg cat gtc aac ttc aag gac atg ggc      96
Ala Arg Cys Ser Arg Lys Ala Leu His Val Asn Phe Lys Asp Met Gly
            20                  25                  30 tgg gac gac tgg atc atc gca ccc ctt gag tac gag gct ttc cac tgc     144
Trp Asp Asp Trp Ile Ile Ala Pro Leu Glu Tyr Glu Ala Phe His Cys
        35                  40                  45 gag ggg ctg tgc gag ttc cca ttg cgc tcc cac ctg gag ccc acg aat     192
Glu Gly Leu Cys Glu Phe Pro Leu Arg Ser His Leu Glu Pro Thr Asn
    50                  55                  60 cat gca gtc atc cag acc ctg atg aac tcc atg gac ccc gag tcc aca     240
His Ala Val Ile Gln Thr Leu Met Asn Ser Met Asp Pro Glu Ser Thr
65                  70                  75                  80 cca ccc acc tgc tgt gtg ccc acg cga ctg agt ccc atc agc atc ctc     288
Pro Pro Thr Cys Cys Val Pro Thr Arg Leu Ser Pro Ile Ser Ile Leu
                85                  90                  95 ttc att gac tct gcc aac aac gtg gtg tat aag cag tat gag gac atg     336
Phe Ile Asp Ser Ala Asn Asn Val Val Tyr Lys Gln Tyr Glu Asp Met
            100                 105                 110 gtc gtg gag tcg tgt ggc tgt agg                                     360
Val Val Glu Ser Cys Gly Cys Arg
        115                 120
```

<210> SEQ ID NO 4
<211> LENGTH: 120
<212> TYPE: PRT
<213> ORGANISM: Homo sapiens

<400> SEQUENCE: 4

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 5
<211> LENGTH: 102
<212> TYPE: PRT
<213> ORGANISM: homo sapiens
<220> FEATURE:
<221> NAME/KEY: MISC_FEATURE
<223> OTHER INFORMATION: cystine-knot domain of GDF-6

<400> SEQUENCE: 5

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 6
<211> LENGTH: 102
<212> TYPE: PRT
<213> ORGANISM: homo sapiens
<220> FEATURE:
<221> NAME/KEY: MISC_FEATURE
<223> OTHER INFORMATION: cystine-knot domain of GDF-7

<400> SEQUENCE: 6

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly

```
                        20                  25                  30

Leu Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                85                  90                  95

Glu Ala Cys Gly Cys Arg
               100

<210> SEQ ID NO 7
<211> LENGTH: 102
<212> TYPE: PRT
<213> ORGANISM: homo sapiens
<220> FEATURE:
<221> NAME/KEY: MISC_FEATURE
<223> OTHER INFORMATION: cystine-knot domain of GDF-5

<400> SEQUENCE: 7

Cys Ser Arg Lys Ala Leu His Val Asn Phe Lys Asp Met Gly Trp Asp
 1               5                  10                  15

Asp Trp Ile Ile Ala Pro Leu Glu Tyr Glu Ala Phe His Cys Glu Gly
                20                  25                  30

Leu Cys Glu Phe Pro Leu Arg Ser His Leu Glu Pro Thr Asn His Ala
            35                  40                  45

Val Ile Gln Thr Leu Met Asn Ser Met Asp Pro Glu Ser Thr Pro Pro
        50                  55                  60

Thr Cys Cys Val Pro Thr Arg Leu Ser Pro Ile Ser Ile Leu Phe Ile
 65                  70                  75                  80

Asp Ser Ala Asn Asn Val Val Tyr Lys Gln Tyr Glu Asp Met Val Val
                85                  90                  95

Glu Ser Cys Gly Cys Arg
               100
```

LIPID MICROPARTICLE GROWTH FACTOR FORMULATIONS

CROSS REFERENCE TO RELATED APPLICATION

This application is a 35 U.S.C. 371 National Phase Entry Application from PCT/EP2007/009198, filed Oct. 23, 2007, which claims the benefit of European Patent Application No. 06 022 159.5 filed Oct. 23, 2006, the disclosure of which is incorporated herein in its entirety by reference.

The present invention is directed to novel formulations and methods for the improved delivery and administration of hydrophobic therapeutic compounds that are substantially insoluble and/or susceptible to precipitation in aqueous solution at physiological pH, including, e.g., growth and differentiation factor-5 and related proteins. Many therapeutic compounds are hydrophobic in the physiological pH range.

As a result, such compounds are substantially insoluble in the physiological pH range in aqueous solutions. Moreover, even those hydrophobic therapeutic compounds that are slightly soluble in aqueous solution at physiological pH, lose this slight solubility, becoming highly susceptible to precipitation when the pH of the solution moves within the physiological pH range.

There are many difficulties with low solubility therapeutic compounds in aqueous solution in the physiological pH range. For example, the power of high-throughput screening for new therapeutic compounds depends upon a match of solubility in aqueous solution at physiological pH and activity. Without sufficient solubility, the compound's activity will not be recognized. Thus, compounds may fail initial testing based on poor solubility, resulting in abandonment of further development efforts. It is estimated that 40% of potential therapeutic compounds fail at screening due to poor aqueous solubility.

Exemplary therapeutic compound growth and differentiation factor-5 (GDF-5) is a morphogen belonging to the transforming growth factor-beta (TGF-beta) superfamily, a group of related proteins with more than 35 different members. TGF-beta superfamily proteins promote cell proliferation and tissue formation and are relevant for a wide range of medical treatment methods and applications. All members of this group are structurally similar and contain a conserved bioactive "cystine-knot" domain comprising six or seven canonical cysteine residues. These dimeric molecules act mainly through specific receptor complexes which are composed of type I and type II serine/threonine receptor kinases. The receptor kinases subsequently activate Smad proteins, which then propagate the signals into the nucleus to regulate target gene expression.

GDF-5 (Flatten et al. 1994, Biochem. Biophys Res. Commun. 204, 646-652), also known as cartilage-derived morphogenetic protein-1 (CDMP-1) or MP52, is very closely related to GDF-6 and GDF-7. These three proteins form a distinct subgroup of the TGF-β superfamily, thus displaying comparable biological properties and an extraordinary high degree of amino acid sequence identity (see i.e. Wolfman et al. 1997, J. Clin. Invest. 100, 321-330).

Besides the prominent functions of GDF-5/-6/-7 in the de novo formation of bone and cartilage (Cheng et al. 2003, J. Bone & Joint Surg. 85A, 1544-1552; Settle et al. 2003, Developm. Biol. 254, 116-130), it has repeatedly been demonstrated that the members of this subgroup are also important inducers and regulators of tendon and ligament (Wolfman et al. 1997, J. Clin. Invest. 100, 321-330), blood vessels (Yamashita et al. 1997, Exp Cell Res. 235, 218-26), nerve tissues (Farkas et al. 1997, Neurosci Lett. 236, 120-122; Watakabe et al. 2001, J. Neurochem. 76, 1455-1464), periodontal ligament and teeth (Sena et al 2003, J. Dent. Res. 82, 166-171; Morotome et al. 1998, Biochem. Biophys. Res. Commun. 244, 85-90), and other tissues and organs. Furthermore, GDF-5 exhibits significant neurotrophic properties, see i.e. Krieglstein et al. 1995, J Neurosci Res. 42, 724-732. Thus, GDF-5 is also a promising agent for the therapy of nerve injuries and neurodegenerative disorders such as Parkinson's disease.

The osteogenic properties of GDF-5 have been successfully used in the past, i.e. to support the healing of local bone fractures. For such purposes, combined osteoinductive materials consisting of GDF-5 and solid carrier matrices have been developed (see for example WO98/21972). However, solid materials are inappropriate for indications, such as osteoporosis, which require a systemic application. Also problematic is drug delivery of the protein to places which are not easily accessible such as the brain or the spinal cord.

In these and similar cases, administration of GDF-5 in soluble form is generally preferred. However, the protein has an isoelectric point of 7.6 and shows exceptionally poor solubility under physiological conditions. Accordingly, previous attempts to formulate stable liquid or gel-like GDF-5 compositions have faced serious problems. A pH-dependent solubility profile of GDF-5/MP52 (shown i.e. in EP 1 462 126) reveals that the protein starts precipitating in aqueous solutions with a pH above 4.25 and becomes completely insoluble between pH 5 and pH 9. Although EP 1 462 126 succeeded in improving the protein solubility profile by using solvents with low ionic strength, solubility at nearly neutral pH has never been achieved but is desirable for parenteral and other formulations.

Due to their unique tissue inductive activities, proteins of the TGF-β superfamily such as GDF-5 have been successfully applied in therapeutic research and regenerative surgery, in which they promote and assist the natural healing process of damaged tissues, either alone or in combination with specific matrix materials. Nevertheless there is still a great need to develop novel methods and formulations for the efficient administration of such proteins under physiological conditions, especially in cases which do not allow the combination of the protein with a voluminous solid carrier material.

Many compounds have therapeutic potential but have limited aqueous solubility at physiological pH. See, e.g., L. Malavolta et al. (2006), Protein Science 15: 1476-1488. (discussing, inter alia, beta amyloid 1-42 which is very soluble at pH 3, but essentially insoluble at pH 7.) ("Many peptide-based drugs with great therapeutic potential are rendered ineffective simply because of an unacceptable propensity for irreversible precipitation.")

It is therefore an objective of the invention to improve the therapeutic qualities of hydrophobic therapeutic compounds with limited aqueous solubility at physiological pH by improving the solubility of such compounds at physiological pH. Another objective is to improve the usability of GDF-5 and related proteins by providing liquid growth factor compositions which are stable, non-toxic and therapeutically applicable at physiological pH values. This objective comprises the development of injectable and/or parenteral formulations, formulations for mucosal administration, slow release compositions, and formulations which can be transported to therapeutic targets which are not easily accessible because of the blood-brain barrier. A third objective of the invention is a method for the preparation of said formulations and compositions. A third objective of the invention is to provide suitable methods for the local or systemic administration of said growth factor compositions. Another objective is the treatment of a number of selected disorders with said formulations and methods.

DEFINITIONS

In order to avoid misunderstandings and ambiguities, some frequently used terms herein are defined and exemplified as follows:

The term "therapeutic compound" as used herein means any agent, substance or composition of substances or therapeutic agents that is administered to an animal or plant as a component of a medical treatment, of any kind including for preventive reasons.

The term "cystine-knot domain as used herein means the well-known and conserved cysteine-rich amino acid region which is present in the mature parts of TGF-beta superfamily proteins such as i.e. human GDF-5 and forms a three-dimensional protein structure known as cystine-knot. In this domain the respective location of the cysteine residues to each other is important and is only allowed to vary slightly in order not to lose the biological activity. It has been demonstrated that the cystine-knot domain alone is sufficient for the biological function of the protein (Schreuder et al. (2005), Biochem Biophys Res Commun. 329, 1076-86). Consensus sequences for cystine-knot domains are well known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 precursor protein (SEQ ID NO: 1) consists of the amino acids 400-501 (see also FIG. 1). For example, the cystine-knot domain of the human GDF-5 precursor protein (SEQ ID NO: 7 and also shown beneath the DNA of SEQ ID NO: 1) consists of the amino acids 400-501 of the GDF-5 precursor protein (see also FIG. 1).

The terms "GDF-5-related protein" as used herein mean any naturally occurring or artificially created protein which comprises a cystine-knot domain with an amino acid identity of at least 60% to the 102 aa cystine-knot domain of human GDF-5 (amino acids 400-501 of SEQ ID NO: 7). This term includes proteins belonging to the group of GDF-5, GDF-6 and GDF-7 proteins from vertebrate or mammalian species as well as recombinant variants thereof as long as these proteins show the above mentioned percentage of identity with the cystine-knot domain of human' GDF-5. The limiting value of 60% is well suitable to separate members of the GDF-51-61-7 group of proteins as well as variants thereof from further proteins such as other GDFs and BMPs. A comparison of the 102 aa cystine-knot-domains of human GDF-5, human GDF-6 and human GDF-7 (see FIG. 2) reveals the high grade of amino acid identity between these proteins. Human GDF-6 shares 87 (85%) and human GDF-7 shares 83 (81%) identical residues with the cystine-knot-domain of human GDF-5. The respective domains of GDF-51-61-7 molecules from other vertebrate and mammalian species which have been identified so far also show very high identity percentages of at least 75% (between 79% and 99%), when compared with human GDF-5. In contrast, GDFs and BMPs not belonging to the GDF-51-61-7 subgroup display much lower identity values below 60% (see FIG. 3).

The determination of corresponding amino acid positions in related amino acid sequences as well as the calculation of percentages of identity between can be easily performed with the help of well-known alignment algorithms and optionally computer programs using these algorithms. The amino acid identities in this patent application have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in:

Thompson, J. D., Gibson, T. J., Plewniak, F., Jeanmougin, F. and Higgins, D. G. (1997)

The ClustalX windows interface: flexible strategies for multiple sequence alignment aided by quality analysis tools. Nucleic Acids Research 24:4876-4882.

ClustalX is a windows interface for the ClustalW multiple sequence alignment program and is i.e. available from various sources, i.e. by anonymous ftp from ftp-igbmc.u-strasbg.fr, ftp.embl-heidelberg.de, ftp.ebi.ac.uk or via download from the following webpage: http://www-igbmc.u-strasbg.fr/BioInfo/. The ClustalW program and algorithm is also described in detail in: Thompson, J. D., Higgins, D. G. and Gibson, T. J. (1994)

CLUSTALW: improving the sensitivity of progressive multiple sequence alignment through sequence weighting, positions-specific gap penalties and weight matrix choice. Nucleic Acids Research 22:4673-4680.

The term "variant" as used herein means any of the following polypeptides:
a) biologically active fragments of a protein
b) protein constructs which contain additional sequences in excess to the original sequence of the protein
c) any combination of a) and b)

The term "colloid" refers to small particles dispersed in a liquid.

The terms "lipid microparticle formulation" and "LMP formulation" refer to homogeneous oil/water microemulsions containing small spherical particles having a particle size below 200 nm.

The term "enhanced solubility" in context with hydrophobic therapeutic compounds, e.g., GDF-5 related proteins, refers to a stabilization of the hydrophobic therapeutic compound, e.g., GDF-5 related protein, in blood and/or aqueous solutions at a pH between 5.0 and 8.5. This stabilization may be achieved by the creation of a stable liquid formulation or aqueous emulsion such as the LMP formulation according to the invention.

The term "physiological pH" as used herein means pH within the range of 4 to 8.5 and more preferably within the range of 5 to 7.5.

The term "biological activity" denotes the activity of therapeutic compounds, including, e.g., a GDF-5-related protein as measured by the common in vitro alkaline phosphatase assay (ALP), e.g. as described in example 2 or in Takuwa et al. (1989), Am. J. Physiol. 257, E797-E803). Suitable cell lines which may be used in such ALP assay are e.g. ATDC-5 or MCHT 1/26 cells.

The term "disorder(s) of the genitourinary system" means disorders affecting the integrity and/or function of one or more of the following organs or parts thereof: male and female sexual organs, prostate, urinary system including bladder, sphincter, anus, pelvic floor muscles, pelvic floor nerves, pelvic floor connective tissues.

The term "sacral nerve(s)" means any one of the sacral nerve(s), portions or branches of the sacral nerve(s), and nerves neurologically connected to any one of the sacral nerves or in close physical proximity thereto.

The term "pudendal nerve(s)" means any one of the pudendal nerve(s), portions or branches of the pudendal nerve(s), and nerves neurologically connected to any one of the pudendal nerves or in close physical proximity thereto.

The term "cavernosal nerve(s)" means any one of the cavernosal nerve(s), portions or branches of the cavernosal nerve(s), and nerves neurologically connected to any one of the cavernosal nerves or in close physical proximity thereto.

The present invention describes novel lipid formulations of that may be applied generally to hydrophobic therapeutic compounds which are generally insoluble in and/or are susceptible to precipitation in aqueous solution in the physiological pH range, e.g., growth and differentiation factor-5 and related proteins. In general, the present invention acts to increase the solubility of hydrophobic therapeutic compounds when they are subjected to physiological conditions, e.g., pH, upon administration.

GDF-5 and the closely related proteins GDF-6 and GDF-7 feature an uncommon surface charge distribution pattern which is associated with an exceptional poor solubility at pH values between pH 4 and pH 9. In contrast to most other hydrophobic proteins, the surface of GDF-5 is not predominantly composed of hydrophobic amino acids such as alanine, valine and leucine. According to the present invention, the limited solubility of GDF-5 appears to be caused by an uncommon charge distribution effect which is shown in FIG. 4. Over a wide pH range, the surface of GDF-5 comprises large regions with opposite charge. These protein parts attract each other and thereby seem to initiate coagulation and precipitation of the growth factor molecule. Only at extremely high or low pH, discharging processes prevent attraction and allow protein solubilization.

The inventors of the present application have proceeded with an extensive investigation in order to overcome the above described problems. Because previous studies already published in EP 1 462 126 showed that solubilization of GDF-5 in different water-based buffers such as sodium acetate does not lead to significant protein solubilities in the desired pH range, various organic hydrophobic solvents have been tested in a first step. Hydrophobic drugs are very often highly soluble in the volatile organic solvents. Surprisingly, no significant solubility of GDF-5 could be achieved in organic solvents even at low or high pH. Results of these experiments are shown in FIG. 5. After adding GDF-5, dichlormethane, acetonitrile and DMSO solutions were centrifuged and the GDF-5 content of the supernatant was checked with RP-HPLC. Retrieval percentages were always below 15%, indicating that only a very small fraction of GDF-5 was in solution.

The present inventors have found that the most efficient way to create active non-toxic formulations of hydrophobic therapeutic compounds, e.g., GDF-5 and related growth factors, which are stable in the physiologic pH range is adhesion to a specific lipophilic colloidal drug carrier of submicron particle size. The interaction between growth factor and the selected nanostructured carrier efficiently prevents the undesired coagulation of the protein at slightly acid/basic and even at neutral pH.

A common feature of all colloidal carriers is their submicron particle size. However, nanometric carriers differ greatly in material, composition, toxicity, drug loading and application spectrum. Because of the anomalous surface charge distribution and other specific characteristics of GDF-5, selection of a colloidal carrier material which is optimized for the GDF-5/GDF-6/GDF-7 family of growth factors is tricky but absolutely imperative. Amongst several others, frequently used colloidal carriers are i.e. liposomes, mixed micelles, lipid microparticles (LMP), and polymeric nanoparticles, which are shortly characterized hereinafter.

LIPOSOMES are very simple structures consisting of one or more lipid bilayers of amphiphilic lipids, i.e. phospholipids or cholesterol. The lipophilic moiety of the bilayers is turned towards each others and creates an inner hydrophobic environment in the membrane. Liposomes are suitable drug carriers for some lipophilic drugs which can be associated with the non-polar parts of lipid bilayers if they fit in size and geometry. The size of liposomes varies from 20 nm to few μm.

MIXED MICELLES are efficient detergent structures which are composed of bile salts, phospholipids, tri, di- and monoglycerides, fatty acids, free cholesterol and fat soluble micronutrients. As long-chain phospholipids are known to form bilayers when dispersed in water, the preferred phase of short chain analogues is the spherical micellar phase. A micellar solution is a thermodynamically stable system formed spontaneously in water and organic solvents. The interaction between micelles and hydrophobic/lipophilic drugs leads to the formation of mixed micelles (MM), often called swallen micelles, too. In the human body, they incorporate hydrophobic compounds with low aqueous solubility and act as a reservoir for products of digestion, e.g. monoglycerides.

LIPID MICROPARTICLES: This term includes lipid nano- and microspheres. Microspheres are generally defined as small spherical particles made of any material which are sized from about 0.2 to 100 μm. Smaller spheres below 200 nm are usually called nanospheres. Lipid microspheres are homogeneous oil/water microemulsions similar to commercially available fat emulsions, and are prepared by an intensive sonication procedure or high pressure emulsifying methods (grinding methods). Simple lipid microspheres consisting of microscopic oil drops in an aqueous dispersion were first investigated for parenteral nutrition (Shenking A. World Rev. Nutr. Diet. 28, 1-111, 1978). Also systems based on aqueous emulsions of soy oil and an outer lecithin (phosphatidycholine) shell were developed (Mizushima Y. Drugs Exptl. Res., XI (9), 595-600, 1985). The natural surfactant lecithin lowers the surface tension of the liquid, thus acting as an emulsifier to form a stable emulsion. The structure and composition of lipid nanospheres is similar to those of lipid microspheres, but with a smaller diameter (Seki et al, J. Controlled Release 28, 352-353).

POLYMERIC NANOPARTICLES serve as carriers for a broad variety of ingredients. The active components may be either dissolved in the polymetric matrix or entrapped or adsorbed onto the particle surface. Polymers suitable for the preparation of organic nanoparticles include cellulose derivatives and polyesters such as poly(lactic acid), poly (glycolic acid) and their copolymer. Due to their small size, their large surface area/volume ratio and the possibility of functionalization of the interface, polymeric nanoparticles are ideal carrier and release systems. If the particle size is below 50 nm, they are no longer recognized as particles by many biological and also synthetic barrier layers, but act similar to molecularly disperse systems.

According to the results disclosed in this patent application (see example 1), the inventors have checked a variety of different nanometric carriers in combination with GDF-5. Whereas several formulations including mixed micelles and organic nanoparticles failed to exhibit the desired effects, the inventors surprisingly succeeded in the identification of optimized lipid microparticle formulations for GDF-5 and related proteins. The preferred LMP formulations of the invention are specifically designed and tested to carry up to 2.5 mg/ml GDF-5 or related proteins at physiological pH (pH 7), which is remarkably high.

There are numerous oils available, which might be used as lipid carriers in a LMP formulation. Synthetic oils are recommendable due to their purity and their known chemical properties. All kinds of synthetic oils can be used as long as they are biocompatible, for example synthetic oils or saturated esters such as ethyl palmitate, isopropyl palmitate, alkyl myristates such as those of isopropyl, butyl and cetyl, hexyl stearate, triglycerides of octanoic and decanoic acids, cetyl ricinoleate, stearyl octanoate (Purcellin oil) and hydrogenated polyisobutene. Due to their well-known biocompatibility and other characteristics, especially common vegetable or plant oils such as e.g. cottonseed, soybean, sesame, sunflower, safflower, olive, avocado, peanut, walnut, almond and hazelnut oils are appropriate in most cases. Various compositions of oils together with emulsifying agents and different protein/LMP ratios were created by the inventors and further compared with respect to solubility and biological activity of the incorporated GDF-5 related growth factor protein.

For ultimate evaluation of the best pre-selected compositions, finally three GDF-5 LMP-formulations comprising olive oil, soybean oil or safflower oil together with different amounts of emulsifying agent phosphatidylserine have been tested regarding bioactivity. In this set of experiments, the alkaline phosphatase (ALP) bioassay and microscopic evaluation of cells treated with empty LMP particles revealed a more or less negative effect of the LMP particles, depending on the oil used. As the integrity of the protein samples has been confirmed, it can be assumed that the reduced bioactivity is not caused by degradation of the growth factor but rather by an inhibitory effect of the LMP on cell growth. Whereas GDF-5 LMP formulations comprising soybean oil or safflower oil demonstrated only medium to low bioactivity levels in comparison to GDF-5 alone, a far better result was obtained using olive oil (see FIG. 8). Thus, the preferred LMP formulations of the invention comprise olive oil. In addition, the formulation comprises also an emulsifying agent. Preferred are phospholipids such as e.g. phosphatidylserine, phosphatidylcholine or phospatidylethanolamine, preferably in the same total amount as the lipid carrier. Other emulsifiers are also possible, e.g. distilled monoglycerides, mono- & diglycerides, acetic acid esters of monoglycerides, organic acid esters of monoglycerides, sorbitan esters of fatty acids, propylene glycol esters of fatty acids and polyglycerol esters of fatty acids.

In another set of experiments, the optimal concentration of oil and emulsifying agent was determined. Three groups of GDF-5 LMP formulations containing low (5-15 mg/ml), intermediate (16-30 mg/ml) and high (31-50 mg/ml) concentrations of oil and identical amounts of emulsifier phosphatidylserine in succinate buffer were tested in the ALP assay system. Although all formulations proved to be bioactive, the activity clearly peaked in the intermediate group (see FIG. 9). According to these results, the preferred LMP formulations of the invention comprise concentrations of oil and/or emulsifying agents between 16 and 30 mg/ml. Most preferred are concentrations between 20 and 25 mg/ml.

The discovered optimized formulations show the following beneficial characteristics:

Avoid precipitation of hydrophobic therapeutic compounds (e.g. GDF-5 related proteins) in aqueous solutions at any pH Allow very high protein load with concentrations up to 2.5 mg/ml Biodegradable and non-toxic for osteocytes, chondrocytes, and neurons Preserve the bioactivity of the protein component Due to nanometric size and excellent biocompatibility, fully injectable or useful for most known delivery techniques such as e.g. dermal, peroral, sublingual, conjunctival, parenteral, ocular, pulmonary, intranasal, topical, and rectal drug delivery Stable at 4° C. for over one month Survive flash freezing in liquid nitrogen Allow storage at −70° C.

According to the invention, said colloidal LMP formulations of the invention can be prepared by a method which comprises the principal steps of a) Initial dissolution of hydrophobic therapeutic compounds (e.g. GDF-5 or related proteins) in aqueous buffers at pH values selected from pH less than 4 or greater than 9 b) Lyophilization of the protein solution c) Preparation of a colloidal drug carrier solution comprising a preselected lipid carrier and an emulsifying agent, and having a pH less than 5 or greater than 9 d) Combination of protein lyophilisate and colloidal drug carrier solution e) Adjustment of the pH of the combined substances to physiologically acceptable values ranging from pH 4.0 to pH 8.5, preferably pH 5 to pH 7.5, most preferably adjustment to pH 7.0.

Because of their small size and biodegradability, lipid microparticles such as the LMP formulations of the present invention can be generally administered by a variety of routes, which are well known in the art. Parenteral administration is currently most demanding and suitable for delivery of such molecules. Subcutaneous, intramuscular or intravenous injection or delivery by an infusion pump is convenient if systemic delivery is desired. Also other administration routes such as oral, dermal, ocular, conjunctival, sublingual, parenteral, rectal, pulmonary, vaginal, topical or intranasal administration are applicable.

The GDF-5 related proteins of the invention include structurally similar proteins comprising a cystine-knot-domain with an amino acid identity of at least 60% to the 102 aa cystine-knot domain of human GDF-5/SEQ ID NO: 7 (for further explanations see also FIGS. 1 to 3). Preferred proteins of the invention have an amino acid identity of at least 70%, 80% or 90% to the 102 aa cystine-knot domain of human GDF-5. The LMP formulations according to the invention are generally applicable in every indication in which GDF-5-related proteins such as GDF-5, GDF-6 and GDF-7 are also useful.

It has been demonstrated in the past that GDF-5-related proteins are indeed multifaceted growth and differentiation factors; they are important inducers and regulators/differentiators of i.e. bone and cartilage (Cheng et al. 2003, J. Bone & Joint Surg. Am. 85-A, 1544-1552; Settle et al. 2003, Developm. Biol. 254, 116-130), connective tissue such as tendon and ligament (Wolfman et al. 1997, J. Clin. Invest. 100, 321-330), nerve tissue (Farkas et al. 1997, Neurosci Lett. 236, 120-122; Watakabe et al. 2001, J. Neurochem. 76, 1455-1464), stem cells (Shimaoka et al. 2003, J. Biomed. Materials Res. Part A 68A, 168-176; Bai et al. 2004, Biochem. Biophys. Res. Commun. 325, 453-460) and periodontal ligament and teeth (Sena et al 2003, J. Dent. Res. 82, 166-171; Morotome et al. 1998, Biochem. Biophys. Res. Commun. 244, 85-90).

Non-limiting examples for vertebrate and mammalian GDF-5 related proteins are: human GDF-5 (disclosed as MP52 in WO95/04819 and as human GDF-5 in Hötten et al. 1994, Biochem. Biophys Res. Commun. 204, 646-652), recombinant human GDF-5/MP52 (WO96/33215), HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol Biotechnol. 16, 203-210), chicken (*Gallus gallus*) GDF-5 (NCBI accession no. NP_989669), african clawed frog (*Xenopus laevis*) GDF-5 (NCBI accession no. AAT99303), monomeric GDF-5 (WO 01/11041 and WO 99/61611), human GDF-6/BMP-13 (U.S. Pat. No. 5,658, 882), mouse GDF-6 (NCBI accession no NP_038554), GDF-6/COMP-2 (WO96/14335), human GDF-7/BMP-12 (U.S. Pat. No. 5,658,882), mouse GDF-7 (NCBI accession no AAP97721), GDF-7/CDMP-3 (WO96/143335). Covered by the invention are also LMP-formulations of GDF-5 related proteins having additional mutations such as substitutions, additions and deletions, as long as these additional mutations do not completely abolish protein activity. Some preferred variants are mutants of GDF-5 related proteins with improved biological activity as described in European patent application no. 05 004 840.4. For example, one or more residues which are normally present in the human GDF-5 precursor proteins (see FIG. 8) are substituted in these mutants by other amino acids: the arginine at position 438 of the human GDF-5 precursor is replaced by glycine, alanine, valine, leucine, isoleucine, methionine or asparagines; and/or serine 439 is replaced by aspartic acid, glutamic acid, glycine, leucine, or isoleucine; and/or asparagine 445 is replaced by serine or threonine. Another high activity mutant is described in European patent application no. 05 025 261.8. In this mutant, methionine 453 and/or methionine 456 are replaced by alanine, valine, or isoleucine. Also of interest are mutants in which leucine 441 is replaced by proline.

Preferably, the LMP formulations of the present invention comprise a vertebrate GDF-5 protein or a variant thereof. This LMP formulation is expected to show the already described activities of GDF-5 or the GDF-5 variant and can be applied wherever the proteins have been successfully used. Some literature which documents the ubiquitous regenerative potential of GDF-5 related proteins is summarized hereinafter.

For example, GDF-5 is considered to be a very effective promoter of bone and cartilage formation as well as connective tissue formation (see for example WO 95/04819, Hötten et al. 1996, Growth Factors 13, 65-74; Storm et al. 1994, Nature 368, 639-643; Chang et al. 1994, J. Biol. Chem. 269, 28227-28234) and formation of connective tissue attachment (EP 0 831 884). In this context, GDF-5 is useful for applications concerning the joints between skeletal elements (see for example Storm & Kingsley 1996, Development 122, 3969-3979). One example for connective tissue is tendon and ligament (Wolfman et al. 1997, J. Clin. Invest. 100, 321-330; Aspenberg & Forslund 1999, Acta Orthop Scand 70, 51-54; WO 95/16035). The protein is helpful for meniscus and spinal/intervertebral disk repair (Walsh et al. 2004, Spine 29, 156-63) and spinal fusion applications (Spiro et al. 2000, Biochem Soc Trans. 28, 362-368). GDF-5 can be beneficially applied in tooth (dental and periodontal) applications (see for example WO 95/04819; WO 93/16099; Morotome et al. 1998, Biochem Biophys Res Comm 244, 85-90) such as the regeneration of dentin or periodontal ligament. GDF-5 is also useful in wound repair of any kind. It is also beneficial for promoting tissue growth in the neuronal system and survival of e.g. dopaminergic neurons. In this context, GDF-5 can be used for treating neurodegenerative disorders like e.g. Parkinson's disease and Alzheimer's disease or Huntington chorea (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). GDF-5 allows animals as well as humans to maintain nervous function or to retain nervous function in already damaged tissues. GDF-5 is therefore considered to be a generally applicable neurotrophic factor. It is also useful for diseases of the eye, in particular retina, cornea and optic nerve (see for example WO 97/03188; You et al. (1999), Invest Opthalmol Vis Sci 40, 296-311), for hair growth and the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

In summary, the LMP formulations according to the invention are for example useful to induce cartilage and/or bone formation, for the prevention or therapy of diseases associated with bone and/or cartilage damage, for spinal fusion purposes, for prevention or therapy of damaged or diseased tissue associated with connective tissue including tendon and/or ligament, for periodontal or dental tissue regeneration, for the fixation of dental implants, for the induction and/or regeneration of neural tissue including PNS and CNS tissue, for the prevention or therapy of neuropathological situations and diseases such as Parkinson's disease, Alzheimer's disease, stroke, multiple sclerosis, neuroAIDS and Lou Gehrig's disease (ALS), for the induction and/or regeneration of tissues of the sensory system, liver, pancreas, cardiac, blood vessel, renal, uterine and thyroid tissue, skin, muscles, mucous membranes, endothelium, epithelium, for promotion or induction of nerve growth, tissue regeneration, angiogenesis, wound healing including ulcers, burns, injuries or skin grafts, induction of proliferation or differentiation of progenitor cells or bone marrow cells, for maintenance of a state of proliferation or differentiation for treatment or preservation of tissue or cells for organ or tissue transplantation, for integrity of gastrointestinal lining, for treatment of disturbances in fertility, contraception or pregnancy.

Due to the dramatically enhanced stabilization of hydrophobic therapeutic compounds such as GDF-5 related proteins in aqueous media at physiologic pH values, the LMP formulations of the invention are especially useful for systemic application approaches. The nanometric dimensions of the lipid carrier facilitate a wide distribution of the protein within the body within minutes after administration. In such cases, the preferred administration mode is subcutaneous, intramuscular or intravenous injection. Delivery by an infusion pump is also adequate. Osteoporosis is a prominent but non-limiting example for a systemic disorder which can be prevented or treated by systemic administration of LMP-formulated GDF-5 or related proteins. The osteogenic and chondrogenic properties of the LMP formulations of the inventions are demonstrated in example 2. Since GDF-5 is a very poor ectopic bone inducer, the protein induces new bone growth mainly in bony tissue but poorly at ectopic sites such as blood, muscles or other organs. Due to this tissue-specific behaviour, LMP-formulated GDF-5 can be injected into the blood and will be distributed via the bloodstream to all bony structures which are damaged by osteoporosis.

Also preferred is the administration of LMP-formulations according to the invention to intervertebral disks, e.g. via injection. It could be shown that GDF-5 and related proteins are capable of inducing regeneration of damaged intervertebral disks, thus restoring functionality of these structures.

In another preferred embodiment, the LMP-formulations according to the invention are especially useful for neuronal regeneration both of the peripheral (PNS) and the central nervous system (CNS). As shown in example 7, lipid microparticles carrying as little as 0.4 µg GDF-5 are capable of healing traumatic nerve lesions and nerve gaps. If the nerve gap is very large, the LMS formulation might be combined with a carrier material. A preferred carrier material is a so-called nerve guide. Nerve guides form a hollow structure, which is able to direct the nerves so that they might find each other.

In an especially preferred embodiment, a method for treating and preventing cellular damages leading to disorders of the genitourinary system and the pelvic floor is disclosed. Such disorders including pelvic pain, urinary/faecal control diseases and disorders of sexual dysfunction adversely affect the health and life quality of millions of people. In these cases, tissue-specific regeneration is mediated by GDF-5 related proteins and can result in functional recovery. Generally all nerves and tissues of the pelvic floor and the genitourinary system can be regenerated with the method disclosed herein. However, especially preferred is the treatment of neuropathic damages related to the sacral, pundendal, and cavernosal nerves. In addition, neovascularization as well as regeneration of muscles and connective tissues such as tendons and ligaments can be achieved. As demonstrated in examples 7A and 7B, these effects can be dramatically enhanced if the GDF-5 related proteins are encapsulated in lipid microparticles.

Two of the most frequent disorders of the genitourinary system are sexual dysfunction and incontinence. In many cases these diseases are associated with injuries of parasympathetic and sympathetic nerve fibres reaching the urogenital tract e.g. through the pelvic, cavernosal and pudendal nerves. For a better understanding, innervation of the pelvic floor and common pelvic floor disorders are shortly described hereinafter.

The cavernosal nerves or erection nerves are formed in the pelvis. They innervate the penis and are responsible for potency. These nerves regulate blood flow during erection as well as detumescence. Specifically, the somatic component (the pudendal nerve) is responsible for the sensations experienced by the penis as well as contraction and relaxation of the extracorporeal striated muscles. Thus, damaged cavernosal nerves are a common cause of impotence. Neurogenic disorders such as Parkinson's disease, stroke, diabetic neuropathies and cerebral trauma often contribute to disorders of erectile function. Frequent causes are also mechanical nerve injuries due to prostatectomies and other abdominal surgeries. In most cases of erectile dysfunction, nerve damage is associated with arterial insufficiency since the penis is a predominantly vascular organ.

Urinary incontinence due to the injury of adjacent nerves often occurs in women after vaginal birth or in men after surgical removal of the prostate gland (prostatectomy). In such cases, incontinence may e.g. result from intrinsic sphincter deficiency caused by reduced or lacking nerve activity. A decrease in urethral closure after vaginal birth can often be ascribed to damage of the pelvic nerves, delayed conduction in the pudendal nerve and denervation of the pelvic musculature. Other causes, which are sometimes collateral to the nerve damages, are injuries of the connective tissues and muscles responsible for maintaining continence.

Sacral nerves are located near the base of the spinal cord in the lower back and control the bladder, bowel and pelvic organs. The sacral plexus supplies innervation to the pelvic muscles, gluteal muscles, and perineal muscles. It also forms the sciatic nerve. The main nerves arising from the lumbosacral plexus are the femoral nerve, obturator nerve, gluteal nerves, caudal rectal nerve and the sciatic nerve and are also treatable according to the present invention.

The pudendal nerve carries sensations from the external genitals, the lower rectum, and the perineum (between the genitals and the anus). Pudendal neuropathy can cause symptoms in any of these areas. A frequent consequence of pudendal neuropathy is incontinence. Some people have mostly rectal pain, sometimes with defecation problems. Others have mostly pain in the perineum or genitals. The symptoms may include stabbing, twisting or burning pain, pins and needles, numbness or hypersensitivity. Usually the symptoms are made worse by sitting, and better by either standing or lying down.

The invention is furthermore useful for the prevention or treatment of vascular damages related to disorders of the genitourinary system. For example, peripheral vascular disease is one of the most common causes of male sexual arousal disorders, e.g. erectile dysfunction, because it is correlated with many systemic diseases which affect the blood vessels of the genital region, directly or indirectly. Chronic diseases such as diabetes mellitus, high cholesterol, high blood pressure, renal failure, heart disease, and others, are very common and lead to the destruction of the contractile walls of the veins or provoke hardening, narrowing or blockages of the arteries leading to the penis. Erection of the penis takes place when blood, carried by the supply arteries of the penis, engorges erectile bodies made of spongeous tissue. Any failure in this filling mechanism, such as the narrowing of arteries by atherosclerotic plaques, may lead to an erectile insufficiency.

Vascular damages are also frequent causes of female disorders of the genitourinary system. Injuries to the vagina during childbirth can cause vascular damage to the vagina and clitoris. Damage to the blood vessels can affect a woman's clitoral, labial, and vaginal sensitivity and her ability to experience sexual arousal and lubrication, and as a result orgasm. Pelvic fractures and other straddles injuries may also affect the pelvic and genital organs and their blood and nerve supplies.

The invention is also useful for the prevention or treatment of muscular or connective tissue damages related to disorders of the genitourinary system. Multiple sclerosis, Parkinson's disease, Alzheimer's disease, stroke, and injury—including injury that occurs during surgery—all can harm bladder nerves or muscles. Regarding connective tissue damages, especially preferred is the treatment of damages of tendons and ligaments. For example, pregnancy and vaginal delivery are considered to be the main risk factors leading to urinary incontinence in women. These two events may cause muscle and ligament damage to the bladder or urethra. Incontinence in women often occurs because of problems with muscles that help to hold or release urine.

According to the regenerative and growth/differentiation effect on pelvic floor/genitourinary nerves, muscles, blood vessels and connective tissues, the present invention is particularly useful for the prevention and therapy of various pathological conditions in which these tissues have been damaged. Non-limiting examples of such conditions are: Male sexual dysfunction, e.g. detractions of ejaculation, detumescence/penile relaxation, penile sensation and contraction of the bulbocavernous and ischiocavernous muscles, impotence or erectile dysfunction (ED), e.g. ED caused by penile arterial insufficiency, veno-occlusive disease, diabetes mellitus and/or damage of the cavernous nerve, ED as a result of surgeries such as prostectomy or cystectomy and prostatic cryosurgery. Female sexual dysfunction, e.g. vaginal engorgement insufficiency and clitoral erection insufficiency caused by nerve damage and/or insufficient blood flow. Tissue damages due to infections or inflammatory diseases of the pelvic floor and urogenital tract, e.g. Balanitis (inflammation of the glans penis), Balanoposthitis (inflammation of the glans and prepuce), urethritis, prostatitis. Incontinence, e.g. urinary, urge and stress incontinence, faecal incontinence, incontinence caused by vaginal distention or surgeries such as e.g. prostatectomies. Pelvic organ prolapse due to damages of ligaments, muscles or nerves, e.g. prolapse of the bladder (cystocele), urethra (urethrocele), uterus, small bowel, rectum. Pelvic pain, e.g pelvic pain due to nerve damages and/or loosened ligaments.

In another preferred embodiment, the discovered lipid microparticle formulation administration methods thereof is optimized for delivery of GDF-5 related proteins to regions of the mammalian body which are protected by the blood-brain barrier. The blood-brain barrier is a capillary endothelial cell lining prohibiting the entry of the majority of solutes present in the blood into the central nervous system.

Inflammation in the brain is a double-edged process that may be beneficial in promoting homeostasis and repair, but can also result in tissue injury through the damaging potential of inflammatory mediators. Thus, control mechanisms that minimize the extent of the inflammatory reaction are necessary in order to help preserve brain architecture and restore function. Multiple sclerosis (MS), NeuroAids and other chronic CNS inflammatory diseases are neurodegenerative disorders whereby chronic destruction of the brain parenchyma results from an autoaggressive, immune-mediated inflammatory process and insufficient tissue regeneration. Because HIV-1 is highly localized within perivascular and infiltrated parenchymal blood-derived macrophages and microglia, it is advisable to target both the lymphatic system and the perivascular spaces of the cerebrovasculature in addition to the brain parenchyma to treat and prevent neuroAIDS and the neurodegeneration and neuroinflammation it entails.

A high concentration of neurotrophic GDF-5 related proteins in central nervous system (CNS) suppresses disease-mediated inflammation and provides neuroprotection by switching the immune response to an anti-inflammatory, suppressive mode in a brain-specific environment. In addition to targeting the CNS, the intranasal delivery method along the trigeminal route also targets the nasal associated lymphatic tissues (NALT), the deep cervical lymph nodes and the perivascular paces and blood vessel walls associated with the cerebrovasculature. Thus, intranasal administration of neurotrophic GDF-5 related proteins can be efficiently used for the treatment and/or prevention of NeuroAids and other neuroinflammatory disorders such as multiple sclerosis (Hanson and Frey 2007, J. Neuroimmune Pharm 2(1), 81-86).

One way to deliver the LMP-formulations according to the invention to the CNS is intracerebral infusion, a method which has been used for the delivery of other growth factors such as GDNF. However, such technique is invasive and risky because cerebral infections are always possible. Thus, the preferred method for delivering GDF-5 related proteins into cells of the central nervous system of mammals (i.e. brain, brain stem and/or spinal cord) is intranasal administration. This method (which is demonstrated in example 6 comprises the steps of a) providing a composition comprising a GDF-5 related protein, and b) contacting said composition with the olfactory region of the nasal cavity, or in an intranasal or an extranasal tissue that is innervated by the trigeminal nerve, wherefrom the GDF-5 related protein is delivered to the CNS.

The basic delivery method through or by way of an olfactory pathway or through or by way of a trigeminal nerve pathway is disclosed in WO 91/07947 and WO 00/33814. However, both applications are completely silent about the specific formulation and delivery of substances with unconventional solubility profile such as GDF-5 and related proteins. Example 6 demonstrates that intranasal administration of GDF-5 related proteins can be dramatically enhanced if the protein is formulated in lipid microparticles.

Agents delivered through or by way of an olfactory pathway can utilize either an intra- or an extracellular route. For example an agent may travel along or within an olfactory neural pathway or an olfactory epithelium pathway to access the CNS. Once the formulation of GDF-5 related proteins is contacted with the nasal cavity, particularly with its upper third, the drug is transported through the nasal mucosa and travels along olfactory nerves into the CNS. Thus, said delivery of GDF-5 related protein formulations to the CNS or brain can i.e. be done by contacting the formulation with the nasal cavity, preferably with the upper third of the nasal cavity.

Alternatively, GDF-5 related proteins may be delivered through or by way of tissues innervated by a trigeminal nerve or one of its branches (i.e. ophthalmic nerve, maxillary nerve, and mandibular nerve). When substances such as e.g. GDF-5 are formulated as a LMP, they become more viscous and stick to the respiratory epithelium in the lower part of the nasal cavity. This is beneficial if a targeting to the midbrain is desired, e.g. to treat Parkinson's disease, because such transportation occurs primarily from the lower part of the nasal cavity along the trigeminal neural pathway.

The trigeminal nerve and its branches innervate not only the entire nasal mucosa but also tissues outside the nasal cavity including skin of the face and scalp, oral tissues, and tissues of and surrounding the eye. Thus, suitable tissues include both intranasal tissue located within the nasal cavity and extranasal tissues such as oral tissues, dermal tissues, or conjunctival tissues, for example skin, epithelium, or mucosa of the face, the eye, the oral cavity, the sinus cavities, or the ear. The drug can be administered transdermally or sublingually and transported along the trigeminal nerve pathway to reach the CNS. After contact with skin innervated by the trigeminal nerve or under the tongue, the agent may be transported through the skin or across the lingual epithelium and travel along trigeminal neurons into areas of the CNS.

As demonstrated in example 6, the LMP-formulations according to the invention are suitable to deliver high amounts of GDF-5 related proteins to the CNS. Therapeutically effective concentrations of GDF-5 were observed in the olfactory bulb (0.6 nM) and trigeminal nerve (3.5 nM) indicating that delivery to the CNS occurs along both the olfactory and trigeminal pathways. Brain concentrations ranged between 0.14 nM and 0.51 nM. Upper cervical spinal cord, as well as ventral and dorsal dura, also contained a high concentration of GDF-5. Therapeutic targets for CNS disorders such as Parkinson's and Alzheimer's disease, the midbrain and hippocampus contained 0.26 nM and 0.15 nM GDF-5 respectively. High delivery to the trigeminal nerves and associated caudal brain regions was observed. As expected, the cervical nodes had high concentrations of GDF-5 (3.5 nM) as a result of drainage from the nasal associated lymphatics. Of the internal organs, the kidneys had the highest concentration of GDF-5 (1.3 nM). It is remarkable that intranasal GDF5-LMP results in higher delivery to the trigeminal nerve, dorsal and ventral dura, than to either the blood or kidney. Delivery to all CNS regions after intranasal administration of GDF-5 was much greater with the LMP formulation than with the aqueous NaAc solutions. Midbrain concentrations were increased almost nine-fold with the use of LMP, and hippocampus concentrations were increased five-fold. Blood concentrations were higher with GDF5-LMP, but even taking that into account, we observed disproportionately greater delivery to caudal structures including the pons, midbrain, cerebellum, and upper cervical spinal cord.

The invention is also particularly suitable for the prevention and treatment of lysosomal storage diseases. Lysosomal storage diseases are caused by a lack of enzymes that normally eliminate unwanted substances in the cells of the body. The enzymes are found in sac-like structures in cells called lysosomes. Lysosomes act as the "recycling center" of each cell, breaking down unwanted material into simple products for the cell to use to build new material. The lack of certain enzymes causes a build-up of the substance that the enzyme would normally eliminate, and deposits accumulate in many cells of the body. Abnormal storage causes inefficient functioning and damage of the body's cells, which can lead to serious health problems. There are more than 40 known lysosomal storage diseases, including:

Fabry disease (Anderson-Fabry disease)—causes kidney and heart problems, pain and a skin rash Gaucher disease—causes the spleen to enlarge, anemia and bone lesions if untreated Hurler syndrome—causes deformities of the skeleton and facial features, enlargement of the spleen and liver, joint stiffness, clouding of the cornea, mental retardation and deafness Niemann-Pick B disease—leads to enlargement of the spleen and liver, as well as lung disease Pompe disease—an often fatal storage disease in which glycogen builds up in the liver, heart and muscle, especially during infancy (also known as acid maltase deficiency)

Tay-Sachs disease—a lysosomal storage disease that occurs more commonly in people of Eastern European Ashkenazi descent and causes degeneration of the brain in infants.

Alpha-galactosidase A deficiency

Angiokeratoma corporis diffusum universale

As discussed above, the invention as described herein is applicable to a broad array of hydrophobic compounds that are insoluble in aqueous media, many of which have therapeutic properties. By way of example, beta amyloid 1-42 is very soluble in aqueous solution at pH 3, but has very low solubility in aqueous solution at physiological pH, e.g., pH 7.4. See L. Malavolta et al (2006), Protein Science 15: 1476-1488.

Thus, the present invention may be used to increase solubility of the following hydrophobic compounds, which have low solubility at physiological pH:

oils; phospholipids; proteins such as certain enzymes, membrane enzymes, lipoproteins and receptors; peptides, including peptide-based drugs; therapeutic small molecules such as antioxidants; anti-inflammatory compounds; biofla-vonoids; glycolipids; porphyrins; steroid sex hormones; antivirals, antibiotics; antidepressants; anxiolytics; antipsychotics; chemotherapeutic compounds.

Specific compounds that may benefit from the present invention include, without limitation, neutraceuticals, myricetin, Vitamin A, Vitamin E, selenium, estrogen, progesterone, testosterone, ceramide trihexosidase, and neutral sphingomyelinase.

The present invention may increase viscosity of the therapeutic compound in a pharmaceutical composition so that delivery of the composition is reduced to the olfactory epithelium, olfactory bulbs and rostral brain structures. In this embodiment, the therapeutic compound, via the pharmaceutical composition of the present invention, is targeted to one or more of the following: respiratory epithelium, trigeminal nerve, caudal brain structures, upper spinal cord, meninges and lymphatics. Significantly, the increased viscosity of the therapeutic compound may allow targeting of the respiratory epithelium, trigeminal nerve, caudal brain structures, upper spinal cord, meninges and lymphatics for soluble therapeutic compounds as well and, as a result, is well within the scope of the present invention.

Moreover, the pharmaceutical composition of the present invention may be administered intranasally, intranasally to the upper third of the nasal cavity, orally, transdermally, to ocular tissues, connjuctival tissues, sublingually, parenterally, rectally, to the pulmonary tissues, vaginally and/or topically. Further still, the pharmaceutical composition of the present invention may be administered by an infusion pump by a deliver and/or injection route that is subcutaneous, intramuscular and/or intravenous in nature.

Thus, the inventive pharmaceutical composition may be administered to the patient's systemic circulation, lymphatics, trigeminal nerve, olfactory nerve and/or the central nervous system including the upper spinal cord and brain.

Various embodiments of the present invention may thus be used to provide pharmaceutical compositions to prevent and/or treat Parkinson's disease, with certain embodiments as discussed above, targeting the midbrain.

Various embodiments of the present invention may be used to prevent and/or treat cerebrellar ataxia, wherein certain embodiments target the cerebellum as discussed above.

Further, various embodiments of the present invention may be used to treat spinal cord injury and/or brain injury, wherein certain embodiments target the spinal cord and/or the brain.

Additional embodiments of the present invention may be used to treat brain stem glioma, with targeting of the brain stem. Moreover, various embodiments may be used to prevent and/or treat trigeminal pain disorders, with targeting of the trigeminal nerve.

Still other embodiments of the present invention may be used to treat central nervous system disorders, comprising generally neurodegeneration resulting from Parkinson's disease, Alzheimer's disease, amyotrophic lateral sclerosis (ALS), multiple sclerosis and Huntington's disease, as well as traumatic brain injury and/or spinal cord injury, ischemia and/or stroke.

Additional beneficial components of a pharmaceutical composition, which is delivered through or by way of an olfactory pathway are odorants. Odorants have high affinity to odorant binding proteins which bind small lipophilic molecules and can act as carriers to olfactory neural receptors. The odorant receptor neurons are localized in the upper part of the nasal cavity in the olfactory epithelium. For more information about odorants and its receptors see i.e. Mori (2003) Biochem. Soc. Transactions 31, part 1, 134-136, and Snyder et al. (1988) J. Biol. Chem. 263: 13972-13974.

Preferably, the odorant according to the invention should be capable of associating with lipophilic substances such as lipid microparticles to further enhance delivery of the hydrophobic therapeutic compounds, including GDF-5 related proteins. Suitable odorant agents are i.e. stimulators of odorant-sensitive enzymes such as adenylate cyclase (see Lowe et al. (1989), Proc. Natl. Acad. Sci. USA 86, 5641-5645), and guanylate cyclase. Further suitable odorants are i.e. esters such as octyl isovalerate, terpanoids such as cetralva and citronellol, aldehydes such as amylcinnamaldehyde, jasmines such as CIS jasmine and jasmal, and musk 89.

The LMP formulations might also comprise another protein which shows synergistic effects if combined with a hydrophobic therapeutic compound of the invention. Preferred additional proteins are GDNF, neurotrophins, hedgehog proteins and proteins of the transforming growth factor family, including but not limited to TGF-alpha's, TGF-beta's, activins, BMP's and GDF's.

Other acceptable components in the pharmaceutical composition according to the invention include, but are not limited to, buffers, stabilizers, preservatives, reducing agents, anti-oxidants and/or anti-oxidant chelating agents, agents that modify isotonicity, adjuvants and solubility-enhancing additives. Especially preferred antioxidants are Vitamin C, Vitamin E and bioflavonoid compounds. These are only examples of possible additives, and a worker skilled in the art can easily add other excipients, which are in use in pharmaceutical preparations or which are generally regarded as safe. For more information about methods for formulating a pharmaceutical composition and selection of pharmaceutically acceptable substances please see Remington's Pharmaceutical Sciences (luth ed.; Mack Publishing Company, Eaton, Pa., 1990), Wang et al. (1980), J. Parent. Drug Assn. 34 (6): 452-462 (1980); Wang et al. (1988), J. Parent. Sci. and Tech. 42: 4-26; Lachman et al. (1968), Drug and Cosmetic Industry 102(1): 36-38, 40 and 146-148; and Akers (1988) J. Parent. Sci. and Tech. 36 (5): 222-228.

In a preferred embodiment of the invention, the LMP formulations can be prepared under $N_2$ (g) using buffers bubbled with $N_2$ (g) to remove dissolved oxygen or to use a vacuum to remove dissolved gases and protect the LMP lipid components and the GDF-5 related protein from oxidation. Alternatively, other inert gas such as argon might be used.

The following non-limiting examples together with the figures and sequence protocols are intended to further illustrate the invention.

SEQ ID NO: 1 shows the DNA and SEQ ID NO: 2 shows the protein sequence of the human GDF-5 precursor.

SEQ ID NO: 4 shows the protein sequence of the human mature monomeric GDF-5.

FIGURES

FIG. 1 shows additional features of the human GDF-5 precursor protein according to SEQ ID NO: 2:
aa 001-381 pre-prodomain (bold letters)
aa 001-027 signal peptide (bold and underlined)
aa 382-501 mature protein part aa [SEQ ID NO: 4]
400-501 cystine-knot-domain (underlined) [SEQ ID NO: 7].

FIG. 2 shows a comparison of the 102 aa cystine-knot domains of human GDF-5 (SEQ ID NO: 7 and also shown with SEQ ID NO: 1), human GDF-6 (SEQ ID NO: 5 and same as aa 19-120 of sequence 26 from U.S. Pat. No. 5,658,882) and human GDF-7 (SEQ ID NO: 6 and same as aa 3-104 of sequence 2 from U.S. Pat. No. 5,658,882). Amino acid residues which are identical in all three molecules are highlighted by borders.

FIG. 3 shows a table with the sequence identities of cystine-knot domains of several known BMPs and GDFs to the cysteine-knot-domain of human GDF-5.

FIG. 4 demonstrates the electrostatic charge pattern of GDF-5 dimer at neutral pH. Regions with similar charge show identical colours.

FIG. 5 shows the poor solubility of GDF-5 in organic solvents. After adding GDF-5, solutions were centrifuged and the GDF-5 content of supernatant was checked with RP-HPLC. Retrieval percentages were below 15%, indicating that only a very small fraction of GDF-5 was in solution.

Figure 8:
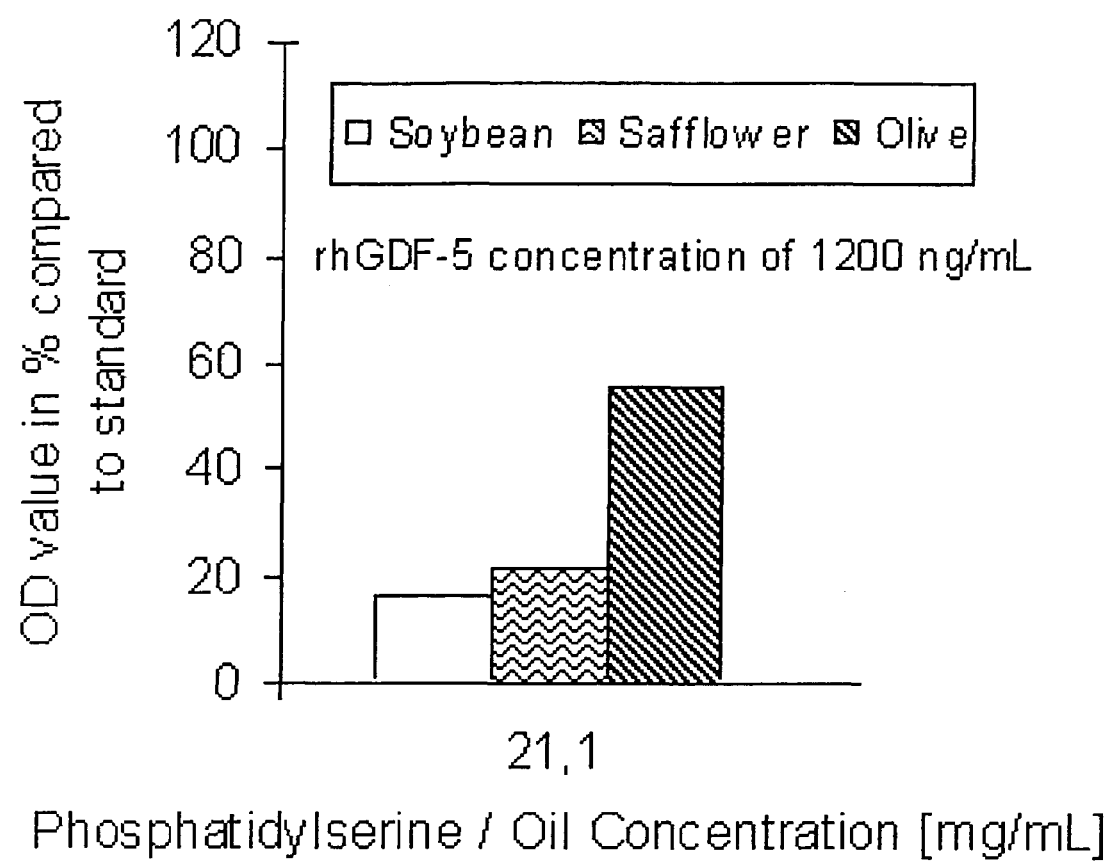

FIG. 8 shows a comparison of the biological activity (measured by ALP assay) of GDF-5 LMP formulations comprising oil selected from soybean, safflower or olive oil and emulsifier phosphatidylserine at concentrations of 21.1 mg/ml. The LMP formulation with the highest bioactivity contains olive oil. OD=optical density.

Figure 9:
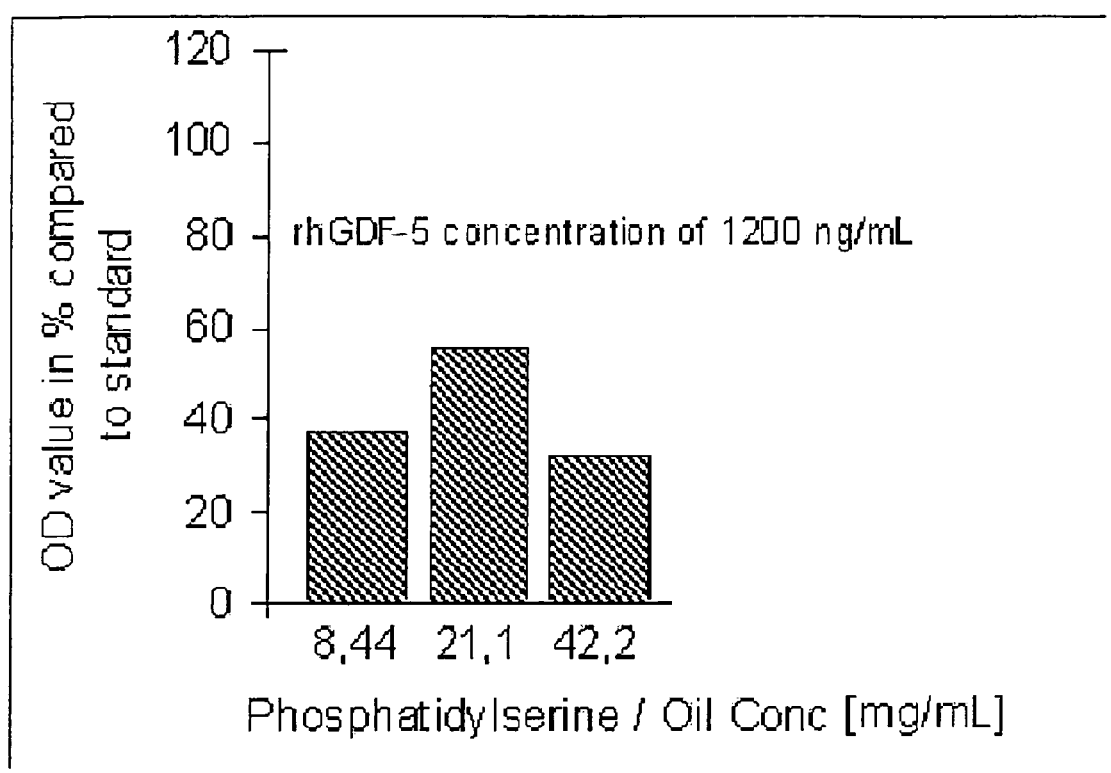

FIG. 9 shows a comparison of the biological activity of three groups of GDF-5 LMP formulations comprising different concentrations of phosphatidylserine and olive oil (low/group 1: 5-15 mg/ml, represented in the figure by 8.44 mg/ml; intermediate/(group 2: 16-30 mg/ml, represented by 21.1 mg/ml, high/group 3: 31-50 mg/ml; represented by 42.2 mg/ml). The groups were tested in the ALP assay system according to example 2. OD=optical density.

Figure 10:
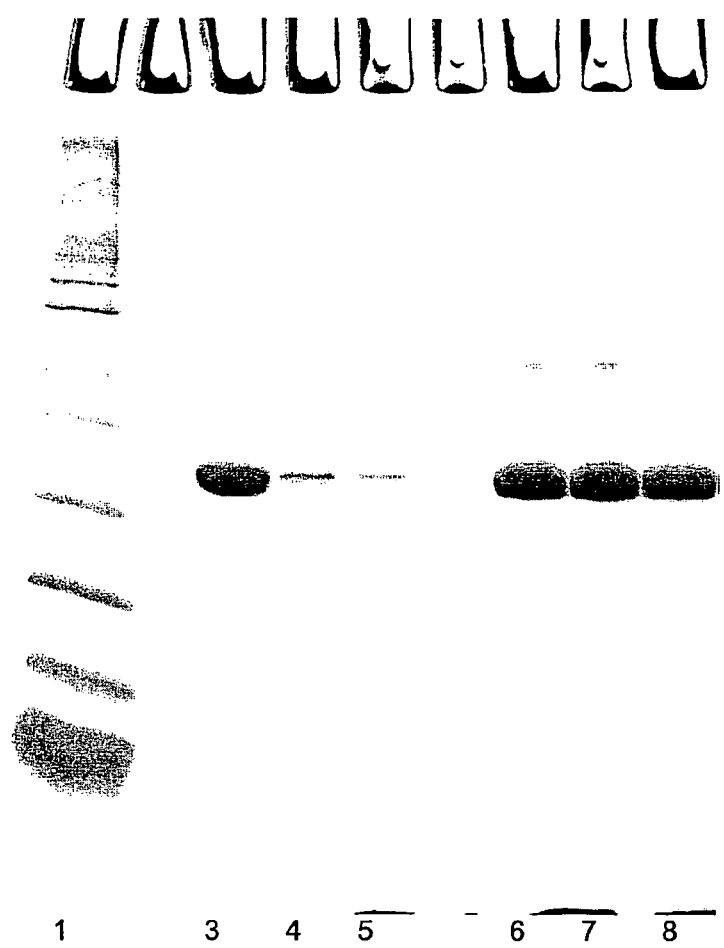

FIG. 10 shows the results of protein size separation via SDS-Page according to example 5. LMP pellets with encapsulated GDF-5 were heated for 10 min at 80° C. to solubilize the lipids. Only very few degradation products are visible, thus demonstrating integrity of most of the GDF-5 protein. Lanes from left to right: 1: Marker protein, 3-5: GDF-5 reference standard 5 µg, 0.25 µg, 0.025 µg, 6-8: GDF-5 LMP samples (5 µg each)

FIG. 11-15 show results of the experiments described in example 6:

FIG. 11 shows a comparison of GDF-5 concentrations (nM) in CNS and various other regions after intranasal administration of three formulations (two aqueous formulations in 20 and 200 mM NaAc pH 4.0 versus the LMP formulation (ph 7.0) as described in example 6.

FIG. 12 shows GDF-5 concentrations (nM) in CNS and various other regions after intranasal administration of the LMP formulation.

FIG. 13 shows a comparison of normalized tissue concentrations of GDF5 after intranasal administration of three formulations. All nM concentrations were normalized to the nmol delivered in the LMP formulation experiments (3.61 nmol).

FIG. 14 shows a comparison of GDF5 targeting to tissues relative to the final blood concentration with different formulations (tissue GDF5/blood GDF5).

FIG. 15 shows a comparison of GDF5 targeting to tissues relative to the muscle concentration with different formulations (tissue GDF5/muscle GDF5).

Figure 16:
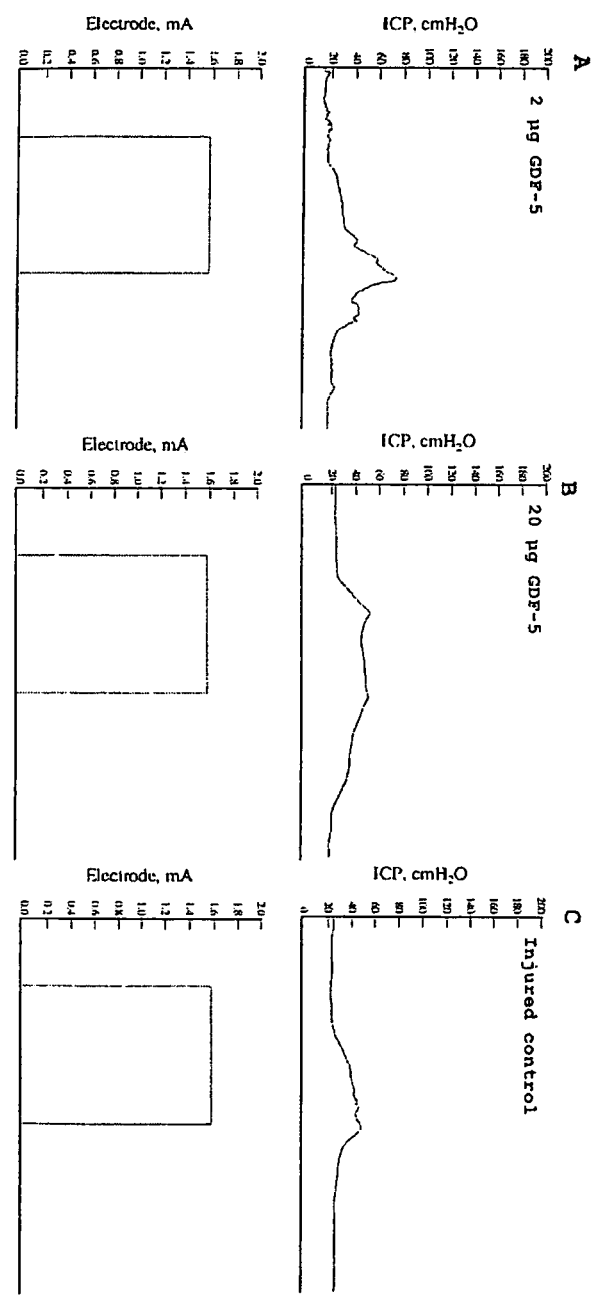

FIG. 16 shows the measurement of intracavernosal pressure (ICP) in rats according to the erectile disfunction/cavernosal nerve crush model described in example 7A (carrier-bound GDF-5). No erectile dysfunction was observed in the uninjured control group (sham surgery group) as evidenced by 149.5+/−17.0 cm $H_2O$ intracavernosal pressure increase (ICP) upon stimulation (diagram not shown). By comparison, ICP decreased seriously in the injured control group (21.3+/−6.7 cm $H_2O$). Groups treated with GDF-5 showed higher recovery than injured control animals After cavernosal nerve injury, maximal ICP increase was obtained with 2 μg carrier-bound GDF-5 (average 40.8+/−13.3 cm $H_2O$).

FIG. 17 shows the results of function testing according to the erectile disfunction/cavernosal nerve crush model described in example 7B (LMP-formulated GDF-5).

FIG. 18 shows nNOS positive nerve fibers in the dorsal penile nerve, and intracorporal apoptosis one month after bilateral cavernous nerve crush injury according to example 7B.

EXAMPLES

Example 1

Development and Testing of Colloidal GDF-5 Formulations

A. Polymeric Nanoparticles

Figure 4:
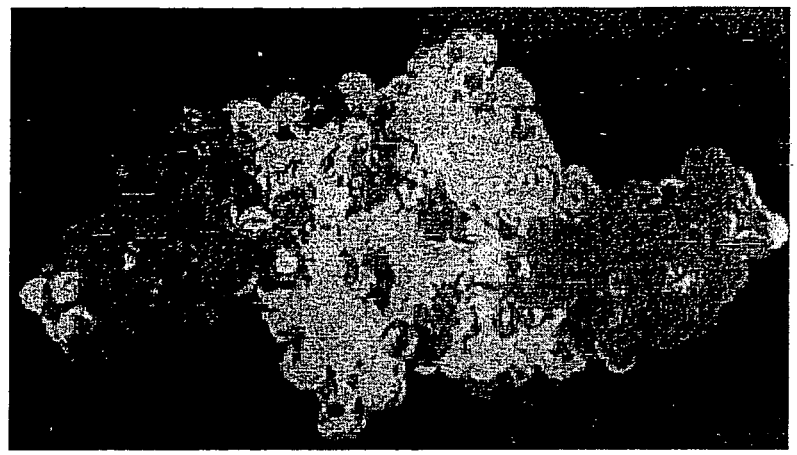
Figure 5:
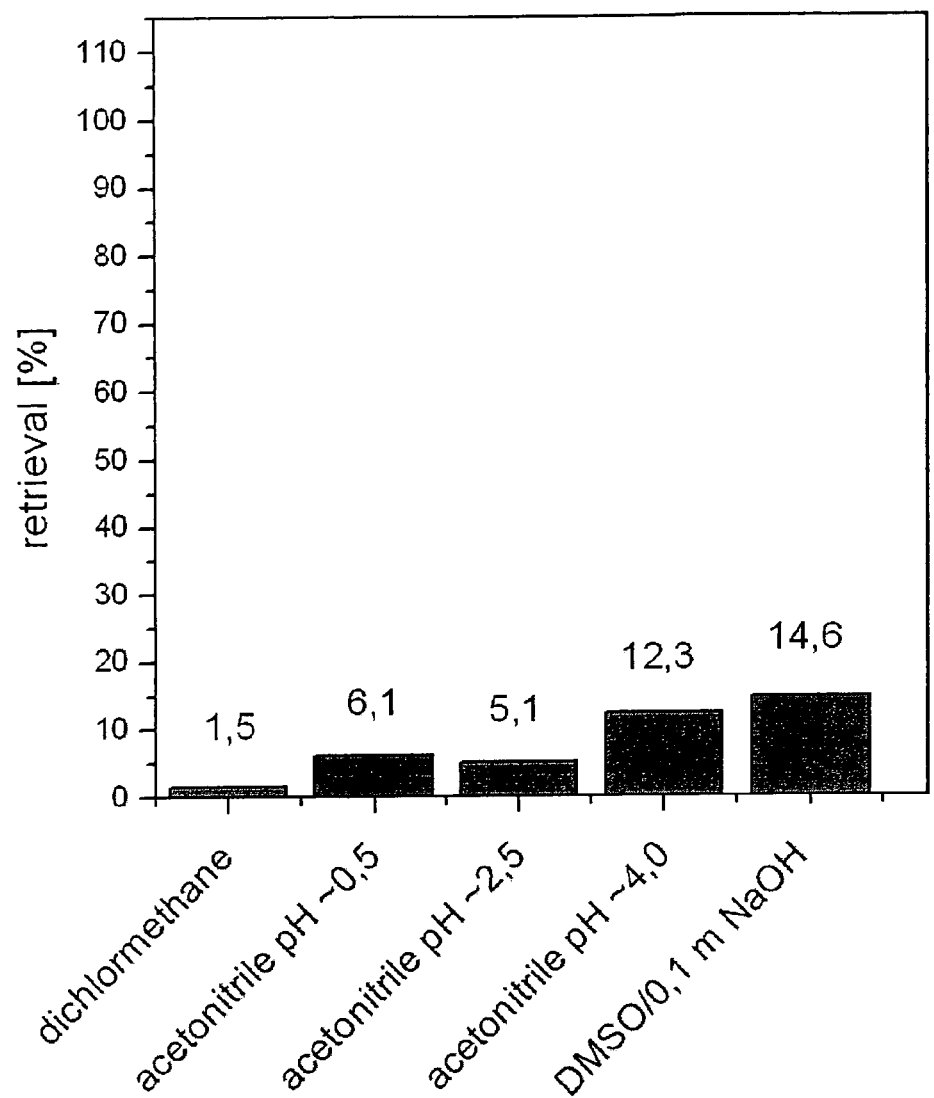
Figure 6:
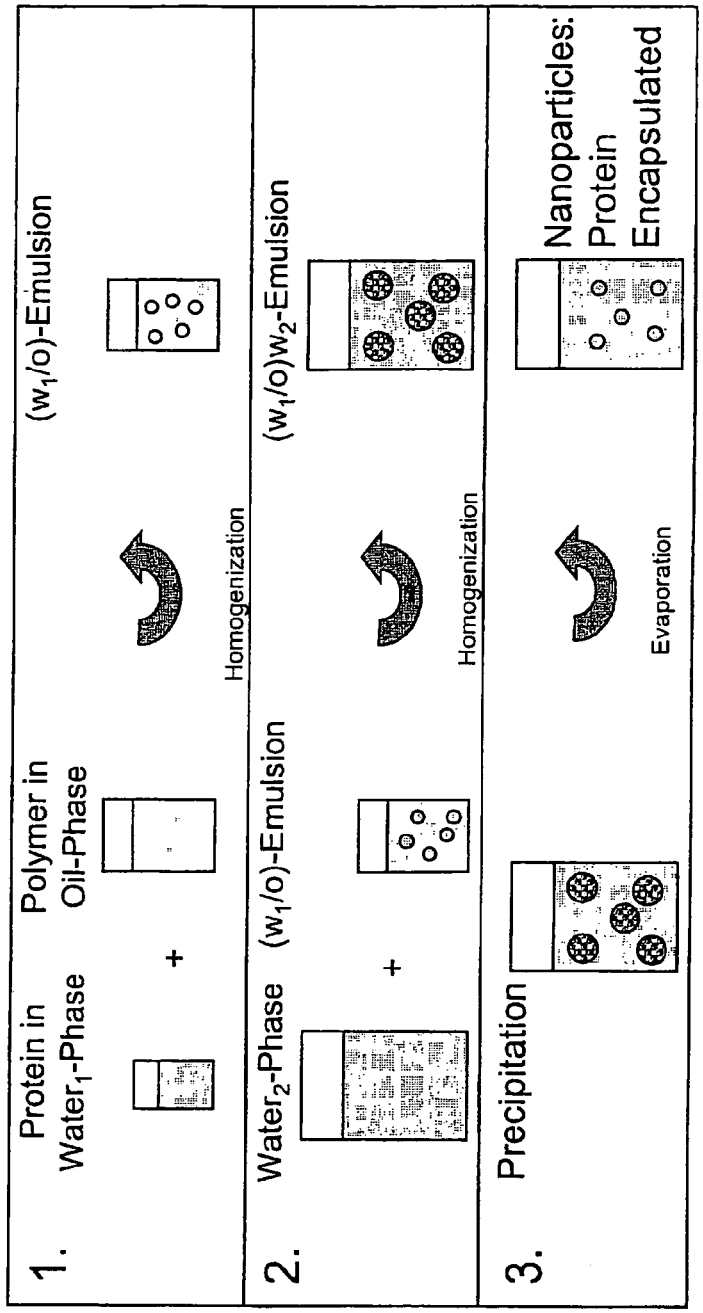
FIG. 6 shows the general synthesis scheme of polymeric nanoparticles (double-emulsion method) as described in example 1 A.
Figure 7:
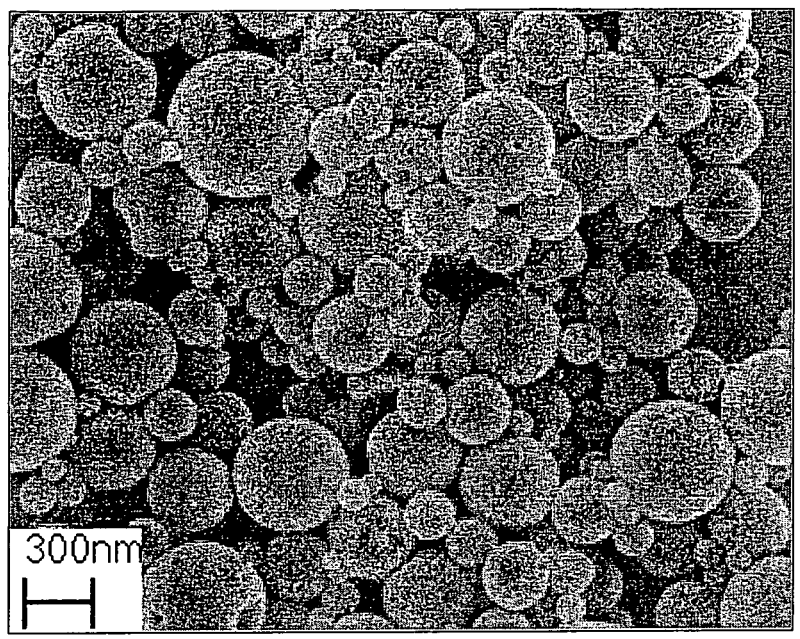
FIG. 7 shows a reflection electron microscopy (REM) picture of Resomer® R202H polymeric nanoparticles according to example 1 A.

Multiple polymeric nanoparticles were tested as colloidal drug carriers for GDF-5, i.e. Resomers® (Boehringer Ingelheim, Germany) with different compositions and molecular weights: PLA Resomers® R202 and R202S (poly-(DL)-lactide), PLGA Resomers® RG502, RG502H, RG503H and RG504H (poly-(DL-lactide-co-glycolide)). As general acidic solvent for GDF-5 10 mM HCl was used, investigated emulsifying agents were polyvinyl alcohol (PVA), poloxamer188 (P188) and polyvinylpyrrolidone (PVP). Synthesis of nanoparticles was performed with the double-emulsion method under sterile conditions according to FIG. 6 (i.e. w1-phase=500 μg protein in 142.1 μl 10 mM HCl, w2-phase=160 mg emulsifier in 30 ml water, o-phase=40 mg polymer in 3.1 ml methylenechloride). Emulsions were created by sonication for 40 sec (w1/0) and 2 min (w1/o/w2), respectively. After removal of the organic solvent by vaporization, precipitation of the polymer and subsequent encapsulation of the protein occurred. Particle size was determined with the help of an electron microscope. Resomer® R202H particles (FIG. 7) combined with emulsifier polyvinyl alcohol or poloxamer188 gave the best results concerning particle morphology and protein load. Average size particles loaded with GDF-5 was approximately 320 nm, average drug concentration 66 μg per mg particle. However, the measured content of encapsulated GDF-5 was determined to be to low for achieving the desired pharmacological effects. In addition, in vitro treatment of mammalian cells (osteo/chondroprogenitor cell line MCHT 1/26) with 1:20 and 1:200 dilutions of GDF-5 nanoparticles in cell culture media resulted in significant cell damage. Due to low protein load and high cytotoxicity, the tested organic nanoparticles were considered to be inappropriate drug carriers for GDF-5 related proteins.

B. Mixed Micelles

Mixed micelles (MM), another potential drug carrier for GDF-5 related proteins, were also tested for drug loading capacity and prevention of precipitation of GDF-5 above pH 4.25. For example, 1 ml MM containing equal amounts of oleic acid and phosphatidylserine in 50 mM succinate buffer (pH 4.25) was transferred in a tube containing 2.5 mg of lyophilized GDF-5. The sample was vortexed for 30 seconds and then sonicated with an average power output of 10 watts for 5 minutes to achieve combination of MM and protein. The mixture was vortexed while 10 μl of 0.5 M NaOH was added to the solution. 10 μl were removed and put onto a pH strip for pH testing. The steps of NaOH addition and pH testing were repeated until the pH reached pH 7.0. As soon as NaOH was added protein started visibly precipitating. The amount of precipitation increased as the pH was raised. At pH 6.0 the amount of precipitation stopped increasing. The sample was centrifuged at 14,000 revolutions per minute, and it appeared that all of the protein had fallen out of solution. The precipitation happened in direct relation to the change of the pH as the solution got cloudier as more NaOH was added. Repeated testing of MM yielded the same results. It was concluded that the tested MM formulations could not solubilize and stabilize GDF-5 above pH 4.25.

C. Lipid Microparticles (LMP):

Several lipid microparticle compositions were created and tested as colloidal drug carriers for GDF-5. For example, 22.93 μl olive oil (21.1 mg) was combined with an equal weight of phosphatidylserine into a 1.5 ml microcentrifuge tube. 956 μl of 50 mM succinate buffer, pH 4.25, was added to bring the total volume to 1 ml. The mixture was vortexed for 30 seconds and placed in an ice-ethanol bath to keep the temperature constantly at 4° C. The sample was sonicated for one hour with an average power output of 22 watts on a 25% duty cycle with a cycle period of 20 seconds. After 1 hour, the emulsion appeared transparent with an amber colour when held up to the light, indicating that the emulsion spheres were getting smaller and reached the expected diameter of approximately 50 nm. At this point, the LMP mixture was transferred by pipette into a microcentrifuge tube containing 2.5 mg of the lyophilized GDF-5 protein. The sample was vortexed until the protein became solubilized. Introduction of the protein caused the mixture to become opaque, indicating a partial disruption of the LMP. The LMP mixture was then sonicated under the same conditions for an additional 45 minutes, restoring the previous transparency. At this point, the lipid microparticle mixture was vortexed on a low setting while 0.5 M NaOH was added in 10 μl increments until pH 7.0 was reached. The pH was measured by placing a small amount of solution on a pH strip. No precipitation was noted during the titration, indicating that the lipid microparticle composition was suitable to carrying high amounts of GDF-5 (up to 2.5 mg/ml) even at neutral pH.

The protein content of the lipid microparticles loaded with GDF-5 was determined via bicinchoninic acid (BCA) assay (Smith, P. K. et al. (1985), Anal. Biochem. 150, 76-85). GDF-5 concentration was of the expected order (around 2.5 mg/ml).

Example 2

Alkaline Phosphatase (ALP) Testing of Biological Activity

The biological activity of GDF-5-related proteins and colloidal formulations thereof can be easily determined with the help of established test systems. Most useful and preferred is the common alkaline phosphatase (ALP) assay (Takuwa et al. 1989, Am. J. Physiol. 257, E797-E803). In this in vitro test system, the biological activity of GDF-5 related growth factors is measured after co-culture of different concentrations (0, 14.8, 44.5, 133.2, 400, 1200 ng/mL) of growth factor protein with osteogenic/chondrogenic cells. GDF-5 and related proteins with osteo/chondrogenic potential increase the alkaline phosphatase (ALP)

expression in these cells, e.g. ATDC-5, ROB-C26 or MCHT-1/26 cells. The ALP activity in these cell lysates is determined by a colorimetric assay. The reaction is based on the hydrolysis of p-Nitrophenylphosphate (PNPP) to p-Nitrophenole, which becomes visible under alkaline conditions as the yellow p-Nitrophenolanion. The aim was to measure the activity of the tested LMP formulations by comparison of the ALP activity obtained with known concentrations of GDF-5 reference standard.

In a standardized ALP assay, $1 \times 10^4$ cells of ATDC-5 or osteo/chondroprogenitor cell line MCHT1/26 cells were incubated overnight in 96-well plates in cell culture medium (alpha-MEM, Penicilline/Streptomycine, 2 mM L-glutamine, 10% FCS) at 37° C., 5% $CO_2$, $H_2O$-saturated. The next day, cells were stimulated with the GDF-5-related proteins or LMP-formulations thereof for 72 hrs with indicated ligand concentrations. The cells were subsequently washed with PBS (phosphate buffered saline). Cell lysis was performed in 100 µl alkaline lysis buffer 1 (0.1M glycine, pH 9.6, 1% NP-40, 1 mM $MgCl_2$, 1 mM $ZnCl_2$) for 1 h at room temperature. Then 100 µl alkaline lysis buffer 2 was added (0.1M glycine, pH 9.6, 1 mM $MgCl_2$, 1 mM $ZnCl_2$+2 mg/ml PNPP). The plates were incubated at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction.

Example 3

RP-HPLC

In order to compare the GDF-5 LMP formulations with a GDF-5 reference standard and to get information about possible aggregation or degradation, a common RP-HPLC analysis of GDF-5 LMP-formulations, able to separate molecules according to their polarity, was used. The chromatography took place at a stationary phase (column: Vydac C18, 5 µm, Phase 218TP52, Protein and Peptide) and a mobile phase under high pressure. The elution of the protein and potential impurities during the chromatography was achieved through a gradient of the mobile phase from polar (0.15% trifluoroacetic acid in water with 35% acetonitrile) to less polar (0.15% trifluoroacetic acid in water with 100% acetonitrile). For the RP-HPLC analysis, the samples were centrifuged for 10 minutes at 13000 g. The supernatants were diluted with 0.15% TFA in 35% acetonitrile. The samples were centrifuged again and the supernatants were applied to the RP-HPLC.

No GDF-5 could be detected in the supernatant, indicating that GDF-5 was completely immobilized with the lipids and it was not possible to analyze those samples by RP-HPLC.

Example 4

Freezing of Lipid Microparticle Formulation

To determine whether the LMP mixture could withstand being frozen, LMP samples were flash-frozen. The sample was submerged in liquid nitrogen for three minutes and then moved directly to a −70° C. freezer and stored for 24 hours. After thawing, LMP showed no visible precipitation and only very little loss of emulsion integrity. The sample was slightly opaque when held up to light which implied a minor disruption of a small part of the microparticles but sonication for 5 minutes completely restored the emulsion. This simple reconstitution method shows the robustness of LMP emulsions.

Example 5

Detection of Protein Degradation

LMP pellets with encapsulated GDF-5 were heated for 10 min at 80° C. to solubilize the lipids, and were processed further via SDS-PAGE. Protein size separation (see FIG. 10) showed only very few degradation products and integrity of most of the GDF-5 protein.

Example 6

Intranasal Delivery of GDF-5 to the Brain

The blood-brain and blood-cerebrospinal fluid barriers prevent the simple intravenous administration of neurotrophins such as GDF-5 for treating CNS disorders such as e.g. Alzheimer's disease or Parkinson's disease. The purpose of these studies was to determine if the GDF-5 could reach the central nervous system (CNS) after intranasal administration. The intranasal delivery method from the nose to the brain uses olfactory and trigeminal neural pathways involved in sensing odors and chemicals. These pathways provide connections between the brain and the external environment without crossing the blood-brain barrier. This example compares intranasal administration of aqueous compositions of GDF-5 related proteins with lipid microparticle formulations thereof.

A. Intranasal Delivery of Aqueous GDF-5 Compositions

In this control study, Male Harlan Sprague-Dawley rats (237+/−4 g) were used. Rats were anesthetized with sodium pentobarbital (50 mg/kg intraperitoneal), and given additional doses as needed. Rats were placed on their back, and body temperature was maintained with a heating pad (rectal thermal probe set at 37° C.). Prior to onset of drug delivery, the descending aorta was cannulated for all experimental groups.

GDF-5 Administration: GDF-5 was $^{125}I$ labelled and formulated in 20 mM sodium acetate buffer at a pH of 4.25. For intranasal administration, a mixture of $^{125}I$-GDF-5 and unlabeled GDF-5 was delivered as 10 µL drops alternating nares every two minutes with an average total volume of 113 µL (7.0 nmol and 38 pCi). A second formulation of GDF-5 for intranasal delivery was prepared in 200 mM sodium acetate buffer at pH 4.0 and delivered as an average total volume of 91 µL (5.2 nmol, 28 uCi). For intravenous administration, a mixture of $^{125}I$-GDF-5 and unlabeled GDF-5 was delivered as an injection into the tail vein. Four intravenous doses were tested (a full IN dose, 1/10th dose, 11/20th dose, and 1/30th dose) using the 20 mM, pH 4.25 formulation. Each injection was a total volume of 500 µL (GDF5 diluted with saline). Blood Collection: After the onset of drug administration, six samples of 0.1 ml blood were collected from the descending aorta. Saline (0.25 ml) was injected through the cannula after every other blood draw to replace volume.

Perfusion and fixation: After drug delivery, rats were perfused through the descending aorta cannula with 60 ml of 0.9% NaCl followed by 350 ml of fixative (4% paraformaldehyde in Sorenson's phosphate buffer). Solutions were delivered at 15 ml per minute.

Measurement of $^{125}I$-labelled GDF-5 with gamma counting: Peripheral and CNS rat tissues were dissected into anatomical areas. Tissues and blood samples were placed in Sarstedt tubes for gamma radiation counting in the Packard Cobra II Auto-Gamma counter. The concentration of GDF-5 in each tissue sample (nM) was calculated using the counts per minute, tissue weight, and specific activity measurements from standard samples of the GDF-5 mixture delivered.

Results are displayed in FIG. 11. While the substantia nigra (within the midbrain) is the principal target for GDF-5 treatment for Parkinson's disease, other targets for treating CNS disorders such as Parkinson's disease include the caudate/putamen, the anterior olfactory nucleus and the olfactory bulb. In summary, results confirmed that GDF-5 can be delivered intranasally to the cerebral CNS. Delivery from the nose to the brain along the olfactory and trigeminal pathways was confirmed by increased but relatively low concentrations in these structures. Intranasal administration of GDF-5 formulated in 20 mM sodium acetate buffer (pH 4.25) resulted in midbrain concentrations of approximately 0.1 nM. Measurements indicated that a significant part of intranasally administered GDF-5 remained directly inside the nares, where it was initially administered. In consequence, GDF-5 was reformulated at a higher buffer concentration and slightly lower pH in order to increase the likelihood that the drug remains in solution when initially contacting tissues at physiological pH. Intranasally administered GDF-5, formulated in 200 mM sodium acetate buffer (pH 4.0), delivered GDF-5 to the brain resulting in a midbrain concentration of 0.25 nM. Intravenously administered GDF-5 resulted in blood exposure that was twice as great as that for intranasally administered GDF-5, but midbrain concentration was less than half. Since neuroprotective effects of GDF-5 have been demonstrated at 1 nM in cultured midbrain neurons, multiple (4 to 6) intranasal doses over time would be required to achieve pharmacologically effective midbrain concentrations of GDF-5. Thus, intranasal formulation studies with LMP formulations were developed and, as shown hereinafter, resulted in much higher delivery and targeting of GDF-5 to the brain.

B. Intranasal Delivery of GDF-5 LMP Formulations

Two experimental changes were made from the previous study of intranasal GDF-5. With the increased viscosity of the GDF-5 LMP formulation, previous tolerability studies indicated that survival was greatly increased with the use of a ketamine cocktail instead of pentobarbital for anesthesia as well as using transcardial perfusion instead of perfusion through cannulation of the descending aorta.

Male Harlan Sprague-Dawley rats (237+/−4 g) were anesthetized with an anesthesia cocktail of Ketamine HCl 150 mg (1.5 mL of 100 mg/mL), Xylazine HCl 30 mg (1.5 mL of 20 mg/mL), and Acepromazine 5 mg (0.5 mL of 10 mg/mL), and given additional doses as needed. Rats were placed on their back, and body temperature was maintained with a heating pad (rectal thermal probe set at 37° C.).

GDF-5 LMP formulation: For individual preparations in 1.5 microcentrifuge tubes, 42.2 mg phosphatidylserine, 45.86 µl (42.2 mg) olive oil, and 912 µl 100 mM succinate buffer pH 4.25 was added. Tubes were vortexed, then sonicated with the probe sonicator, according to the following protocol: a) the sonicator probe tip was placed just above the bottom of the microcentrifuge tube without touching the sides; b) the sample was sonicated in an ice-ethanol bath for one hour at setting 10 on a 25% duty cycle with a cycle period of 20 seconds, producing an average power output of 22 watts; c) the ice-ethanol bath had to be changed approximately every 12 minutes to keep the sample at approximately 4° C.; d) after 1 hour, the emulsion appeared transparent with an amber color when held up to light. 500 µl of the obtained LMP emulsion was transferred into a microcentrifuge tube containing an aliquot of 2.5 mg lyophilized GDF-5. The tube was sonicated for another hour following the same protocol. At this point, equal volumes $^{125}$I-GDF-5 and GDF-5 in LMP were combined. The tube was covered with parafilm and sonicated in the bath sonicator for two hours. Once the radiolabeled GDF-5 was incorporated into the LMP, the sample was titrated up to pH 7.0 with 1 M NaOH. The NaOH was added 10 µl at a time and vortexed while the tube was closed. The pH was determined by pH strips. Doses were aliquoted and flash-frozen until use. On the day of each experiment, $^{125}$I-GDF5-LMP was thawed to room temperature and placed in bath sonicator for 1 hr prior to dosing. $^{125}$I-GDF5-LMP was delivered as 5 µL drops alternating nares every two minutes with an average total volume of 38.5 µL (3.6 nmol and 40 µCi). Total drug delivery time was fourteen minutes.

Perfusion and fixation: Approximately 24 min after the onset of drug delivery, rats were transcardially perfused with 60 ml of 0.9% NaCl followed by 350 ml of fixative (4% paraformaldehyde in Sorenson's phosphate buffer). Solutions were delivered at 15 ml per minute.

Measurement of $^{125}$I-labelled GDF-5 with gamma counting: Peripheral and CNS rat tissues were dissected into anatomical areas. Tissues and blood samples were placed in Sarstedt tubes for gamma radiation counting in the Packard Cobra II Auto-Gamma counter. The concentration of GDF-5 in each tissue sample (nM) was calculated using the counts per minute, tissue weight, and specific activity measurements from standard samples of the GDF-5 mixture delivered.

Results are displayed in FIGS. 11 to 15. In summary, LMP formulation of GDF-5 was stable and was well tolerated by rats when administered intranasally under ketamine anesthesia. Intranasal delivery of GDF-5 to the CNS was rapid (within 28 minutes). High concentrations of GDF-5 were observed in the olfactory bulb (0.6 nM) and trigeminal nerve (3.5 nM) indicating that delivery to the CNS occurs along both pathways. Brain concentrations ranged between 0.14 nM and 0.51 nM. Upper cervical spinal cord, as well as ventral and dorsal dura, also contained a high concentration of GDF-5. Therapeutic targets for CNS disorders such as Parkinson's and Alzheimer's disease, the midbrain and hippocampus contained 0.26 nM and 0.15 nM GDF-5 respectively. In general, GDF-5 concentrations in rostral brain regions (frontal cortex, caudate/putamen, 0.18 nM) were lower than in more caudal brain regions such as pons, medulla, cerebellum (0.5 nM). High delivery to the trigeminal nerves and associated caudal brain regions in comparison to the lower delivery to the olfactory bulb and associated rostral tissues may be due to the high viscosity of the LMP formulation. High viscosity of LMP could increase its adherence to the respiratory epithelium (innervated by the trigeminal nerve), while decreasing the amount that reaches the olfactory epithelium in the upper nasal cavity. As expected, the cervical nodes had high concentrations of GDF-5 (3.5 nM) as a result of drainage from the nasal associated lymphatics. Of the internal organs, the kidneys had the highest concentration of GDF-5 (1.3 nM). It is remarkable that intranasal GDF5-LMP results in higher delivery to the trigeminal nerve, dorsal and ventral dura, than to either the blood or kidney. This data demonstrates that GDF-5, a therapeutic protein with little or no solubility in the physiologic pH range, has been successfully stabilized in aqueous media and delivered to the brain using the disclosed lipid microparticle formulation.

Comparison of the intranasal delivery data obtained with GDF5-LMP to that obtained with the aqueous solutions: It is most relevant to compare the GDF5-LMP data with the 20 mM NaAc data because the ionic strength of the dosing solution is similar. Delivery to all CNS regions after intranasal administration of GDF-5 was much greater with the LMP formulation than with the 20 mM NaAc solution. Midbrain concentrations were increased almost nine-fold with the use of LMP, and hippocampus concentrations were increased five-fold. Blood concentrations were higher with GDF5-LMP, but even taking that into account, we observed disproportionately greater delivery to caudal structures including the pons, midbrain, cerebellum, and upper cervical spinal cord. Increased contact of LMP with the epithelium and increased lipophilicity of the formulation probably contribute to increased blood bioavailability. In virtually every region of the CNS, the ratio of GDF-5 tissue concentrations relative to muscle concentrations (indicative of systemic exposure) was markedly increased with the LMP formulation.

Concentrations of GDF-5 in the olfactory epithelium were approximately twelve-fold lower with LMP as compared to the 20 mM NaAc formulation. However, olfactory bulb concentrations were in fact greater by about two-fold. This suggests that LMP increases the ability of GDF-5 to travel from the nasal epithelium to the olfactory bulb. This may be because the aqueous solutions of GDF-5 were near the pH threshold for solubility (pH 4.3). The rise in pH, when the aqueous solutions contact the nasal epithelium, likely results in greatly decreased solubility of GDF-5. In addition, for GDF-5 to travel along the neural pathways from the nasal cavity to the CNS it must traverse an environment of neutral pH. The LMP formulation provides an environment that stabilizes GDF-5 at neutral pH enhancing its transport from the nasal cavity to the brain.

Example 7

GDF-5 Mediated Angiogenesis and Cavernosal Nerve Regeneration in a Rodent Model of Erectile Dysfunction In order to determine the efficacies/differences of carrier-administered GDF-5 protein in comparison with injected GDF-5 LMP formulations in the healing of nerve damages, a rat model of cavernosal nerve injury was used. The cavernosal nerves or erection nerves are responsible for potency.

A. Carrier-Administrated GDF-5

In this control study, the conventional administration route of GDF-5 protein was used: implantation of a collagen sponge loaded with GDF-5. Four groups with eight Sprague Dowley rats each were used. Group 1 underwent sham surgery (laparotomy-group 1), groups 2 to 4 bilateral cavernosal nerve (nervus cavernosus) crush. The surgery was done under 2-3% isofluorane anaesthesia. Isothermia was maintained at 37° by placing the rats on a heating pad. The prostate gland was exposed through a lower abdominal midline incision. After periprostatic dissection, the cavernosal nerve and the major pelvic ganglion were identified posterolaterally on either side of the prostate. The uninjured controls (sham) had no further manipulation. In the remaining groups, the cavernosal nerves were isolated and crushed for 2 min per side, using a haemostat clamp. Thereafter the penis was exposed and the right corpus cavernosum incised for 2 mm using a surgical blade. A 3×3 mm GDF-5 impregnated collagen sponge containing the appropriate level of GDF-5 was implanted. Groups were: collagen sponge alone (vehicle control/group 2), collagen sponge (3 cm$^3$)+2 µg GDF-5 (low dose group 3), or collagen sponge (3 cm$^3$)+20 µg GDF-5 (high dose/group 4). The corpus cavernosum was closed using an absorbable 7/0 suture. The abdomen was closed in two layers.

Eight weeks after surgery, erectile function was tested by functional studies, e.g. by electrostimulation of the cavernosal nerve and subsequent generation of erections. Stimulation of the cavernosal nerve and monitoring of intracavernosal pressure were performed as described in example 7B.

In summary, application of carrier-bound GDF-5 enhanced recovery of erectile function moderately, with a 2 µg dose demonstrating the most promising results of nerve regeneration. Groups treated with GDF-5 showed higher intracavernosal pressure than injured control animals (see FIG. 16). No erectile dysfunction was observed in the uninjured control group (sham surgery group) as evidenced by 149.5+/−17.0 cm $H_2O$ intracavernosal pressure increase (ICP) upon stimulation. By comparison, ICP decreased seriously in the injured control group (21.3+/−6.7 cm $H_2O$). After cavernosal nerve injury, the recovery of erectile function was greatest in the low concentration (2 µg) GDF-5 treatment group. The maximal ICP increase was 40.8+/−13.3 cm $H_2O$ for 2 µg carrier-bound GDF-5, an increase of 91.5 percent in comparison with the injured control group.

B. Injection of GDF-5 LMP-Formulations

This study was designed to evaluate the beneficial effects of LMP-based GDF-5 formulations. Six groups with eight Sprague Dowley rats each were used. All animals received anesthesia prior to the surgical procedures. Group 1 underwent sham surgery (laparotomy-group 1), groups 2 to 6 bilateral cavernous nerve crush. Group 2 (control) received no formulation at all, groups 3 to 6 received lipid microparticle formulations containing 21.1 mg/ml olive oil, 21.1 mg/ml phosphatidylserine (see example 1 C) and additionally 0 µg (vehicle), 0.4 µg (low concentration), 2 µg (middle concentration) or 10 µg GDF-5 (high concentration).

The surgery was done under 2-3% isofluorane anaesthesia. Isothermia was maintained at 37° by placing the rats on a heating pad. The prostate gland was exposed through a lower abdominal midline incision. After periprostatic dissection, the cavernosal nerve and the major pelvic ganglion were identified posterolaterally on either side of the prostate. The uninjured controls (sham) had no further manipulation. In the remaining groups, the cavernosal nerves were isolated and crushed for 2 min per side, using a haemostat clamp. Thereafter the penis was exposed and 10 µl of lipid microparticle formulation containing different amounts of GDF-5 were injected into the right corpus cavernosum via 33 G needle (Hamilton, Reno, Nev.). The corpus cavernosum was closed using an absorbable 7/0 suture. The abdomen was closed in two layers.

Eight weeks after surgery, erectile function was tested by functional studies, e.g. by electrostimulation of the cavernosal nerve and subsequent generation of erections. After a repeat midline abdominal incision, the cavernosal nerves were exposed and isolated. Next, the penis was isolated and a 23 G butterfly needle inserted into the left crus body to measure the intracavernosal pressure (ICP). The needle, filled with 250 U/ml heparin solution, was connected to a pressure transducer. The ICP was recorded at a rate of 10 samples/s using a sensor input module. A bipolar stainless-steel hook electrode was used to stimulate the cavernosal nerve directly (each pole 0.2 mm in diameter, separated by 1 mm). A signal generator with a custom-built constant current amplifier generated monophasic rectangular pulsed. The stimulus parameters were 1.5 mA, 20 Hz, pulse width 0.2 ms, and duration 50 s. The maximum ICp in each rat was determined as the mean peak ICP of both sides.

Results of function testing (see FIG. 17): Injection of GDF-5 LMP formulation enhanced nerve regeneration and recovery of erectile function dramatically, with a 0.4 µg dose GDF-5 being most effective and showing an increase of 566% in comparison to the injured control group. After consideration of the standard deviation, the maximum ICP values of this group (99.87+/−30.56) do not differ significantly from those of healthy rats (sham group, 111.15+/−29.69). In contrast, ICP decreased seriously in the injured control group (14.99+/−6.78 cm $H_2O$).

Also the other groups treated with GDF-5 showed higher intracavernosal pressure than injured control animals. The maximal ICP increase was 72.11+/−35.8 cm $H_2O$ for 2 µg carrier-bound GDF-5, an increase of 381% in comparison with the injured control group. In the 10 µg GDF-5 group, mean value was 26.92+/−20.16 (+79.6%).

In addition, nerve regeneration as well as significant neovascularization was confirmed histologically/microscopically. To determine the number of neuronal nitric oxide synthase (nNOS)-containing fibers in the dorsal penile nerve, freshly dissected tissue was fixed for 4 h with cold 2% formaldehyde, 0.002% picric acid in 0.1M phosphate buffer, and overnight immersion in buffer containing 30% sucrose. Tissues were frozen in OCT compound and stored at −70° C. until use. Sections were cut at 5 microns, adhered to charged slides, air dried for 5 min, and rehydrated with 0.05M phosphate buffered saline (PBS). Sections were treated with hydrogen peroxide/methanol to quench endogenous peroxidase activity. After rinsing, sections were washed in PBS followed by 30 min room-temperature incubation with 3% goat serum/PBS/0.3% triton X-100. After draining solution from sections, tissues were incubated overnight at room temperature with rabbit polyclonal anti-nNOS (1:800; Cayman Chemicals, Ann Arbor, Mich.). After washing, sections were immunostained using the avidin-biotin-peroxidase method (Elite ABC; Vector Laboratories, Burlingame, Calif.), with diaminobenzidine as the chromogen, followed by hematoxylin counterstaining. The staining was assessed by counting the number of nNOS-positive nerve fibers in the dorsal penile nerve at 400× magnification (perineural staining was not included in the count).

To quantify apoptosis in the penile cavernous tissue, terminal deoxynucleotidyl transferase-mediated dUTP-biotin nick end labeling (TUNEL) was performed according to manufacturer's specifications using the TUNEL apoptosis detection kit (Chemicon, Temecula, Calif.). For image analysis, five randomly selected fields of intracavernous tissue per animal were photographed and recorded at 400× magnification using a Retiga 1300 digital camera (QImaging, Surrey, Canada) attached to a Nikon E300 microscope (Nikon Instruments, Melville, N.Y.). Images were analyzed with Image-Pro Plus 5.1 software (Media Cybernetics, Bethesda, Md.) to quantify the signal.

Histology of the dorsal nerve demonstrated a significant loss of nNOS-positive fibers after crush injury in the injured control group compared to uninjured controls (FIG. 18). GDF-5 treatment preserved nNOS-containing nerve fibers in a dose-dependent fashion. Animals treated with low-concentration GDF-5 had significantly higher numbers of nNOS-positive fibers when compared to injured controls. Animals in the intermediate-concentration group also had more nNOS-positive fibers than injured controls but the difference did not attain statistical significance. There was no significant difference in nNOS staining in the high-concentration group compared to injured controls.

Intracavernous apoptosis was significantly increased after CN crush injury (FIG. 18). GDF-5 injection decreased the number of TUNEL-positive cells in a dose-dependent fashion. Animals treated with intermediate- and low-concentration GDF-5 showed a significant anti-apoptotic effect with low-concentration GDF-5 being most potent. Animals treated with high-concentration GDF-5 demonstrated significantly increased apoptosis when compared to injured controls.

Example 8

Development and Testing of Further Colloidal Formulations

The lipid microparticle compositions of the invention were successfully tested as colloidal drug carriers for mid-size or even large proteins such as e.g. GDF-5 (see example 1). They are also suitable drug carriers for other substances of similar or smaller size which may have divergent chemical and physical characteristics. Some non-limiting examples are shown hereinafter:

In an effort to increase the solubility of several substances to enhance it's therapeutic potential, these substances were incorporated into LMP as follows:

(a) 21.1 mg phosphotidylserine, 22.93 uL (21.1 mg) olive oil, and 956 uL 50 mM succinate buffer (pH 4.25) were added to a 1.5 mL microcentrifuge tube.
b. The tube was vortexed briefly.
c. The sample was placed in an ice-ethanol bath to maintain a temperature of approximately 4° C.
d. The tip of a probe sonicator was placed just above the bottom of the microcentrifuge tube. It was confirmed that the sonicator tip was not touching the sides or the bottom of the tube.
e. The sample was sonicated for 2 h at setting 10 on a 25% duty cycle with a period of 20 sec, producing an average power output of 22 watts.
f. The ice-ethanol bath was changed every 12 min to maintain temperature.
g. After 2 h, the emulsion appeared transparent. When held up to light, the LMP solution appeared amber in color.
h. The solution was centrifuged for 4 min at 12,000 rpm to remove any metal particulates left by the probe tip.
i. 1 ml of the LMP was transferred to a clean 1.5 microcentrifuge tube.

After this step (i.), the substance to be encapsulated was added to the tube (see steps j. to o.), e.g.:

8a. Polyphenols

Polyphenols are a group of chemical substances found in plants, characterized by the presence of more than one phenol group per molecule. The term comprises tannins, lignins and flavonoids. For example, the flavonoid myricetin can be successfully incorporated into the colloidal drug carriers of the invention. Myricetin (C15H10O8, MW 318.24) is a naturally occurring flavonoid found in many food sources known to have antioxidant and anti-inflammatory properties. In vitro research suggests that high concentrations of myricetin may reduce prostate cancer prevalence and modify LDL cholesterol by increasing white blood cell uptake (Knekt et al. 2002 Am. J. Clin. Nutr. 76(3):560-568). Myricetin has also been shown to have anti-amyloidogenic activity and may be helpful in preventing or treating Alzheimer's disease and neurodegeneration (Ono et al. 2003 J. Neurochem 87(1):172-181). Despite its therapeutic potential, myricetin has very limited water solubility. Based on our own results, the solubility of myricetin in water is 0.065 mg/mL. In an effort to increase the solubility of myricetin to enhance its therapeutic potential, myricetin was incorporated into lipid microparticles as follows:

j. 1 mg myricetin was added to the tube and vortexed to combine. The mixture appeared bright yellow and opaque.
k. The myricetin mixture was again placed over the ice-ethanol bath and fitted with the probe sonicator.
l. The mixture was sonicated on the same settings for 2.5 h, again replacing the ice-ethanol bath every 12-15 min.
m. After 2.5 h, the solution appeared golden and transparent.
n. The solution was centrifuged again for 5 min at 12,000 rpm to remove any metal particulates.
o. The solution was then titrated to pH 7 with 1 M NaOH. The golden color deepened and remained completely transparent.

Myricetin was successfully prepared at 1 mg/ml and stabilized at pH 7 using the lipid microparticle formulation. The aqueous solubility of myricetin at neutral pH was increased 15.4-fold using this new formulation. Even higher concentrations of myricetin at neutral pH may be achieved using the LMP-formulation. This greatly improves the therapeutic potential of myricetin as an antioxidant and anti-inflammatory.

8b. Vitamins

In humans there are 13 vitamins which can not be produced by the human body itself: 4 fat-soluble (A, D, E and K) and 9 water-soluble (8 B vitamins and vitamin C) vitamins.

Vitamin E is a fat soluble vitamin that is also an important antioxidant. Chemically, vitamin E contains a hydroxyl group which donates a hydrogen atom and reduces free radicals. Its hydrophobic side chain allows vitamin E to penetrate biological membranes but also leaves it virtually insoluble in aqueous media. Vitamin E occurs in 8 forms: 4 tocopherols and four tocotrienols. In particular, alpha tocopherol is often recognized as the most active form of vitamin E used in humans. A deficiency in humans can lead to neurological problems, among others. Increasing the solubility of vitamin E could increase its therapeutic potential and may also help to solve deficiency problems.

In an effort to increase solubility, Vitamin E was incorporated into lipid LMP as follows:
j. 5 uL (4.65 mg) of vitamin E was added to the tube and vortexed to combine.
k. The Vitamin E mixture was placed over the ice-ethanol bath again and fitted with the probe sonicator.
l. The mixture was sonicated on the same settings for 2.5 h, again replacing the ice-ethanol bath every 12-15 min.
m. After 2.5 h, the solution appeared transparent.
n. The solution was centrifuged again for 4 min at 12,000 rpm to remove any metal particulates.
o. The solution was then titrated to pH 7 with 1 M NaOH. The solution remained completely transparent.

Vitamin E was successfully prepared at 4.65 mg/ml and stabilized at pH 7 using the lipid microparticle formulation. The aqueous solubility of vitamin E at neutral pH was increased greatly using this new formulation. Even higher concentrations of vitamin E at neutral pH may be achieved using the LMP-formulation.

8c. Peptides/Proteins

Peptides and also proteins often show reduced water solubility due to the presence of hydrophobic amino acids such as Phe, Ala, Leu, Met, Ile, Trp and Pro. For example, Leu-Leu-Leu is a tripeptide consisting of three base units of the hydrophobic, essential amino acid Leucine. With a chemical formula of $C_{18}H_{35}N_3O_4$ and a molecular weight of 357.49, Leu-Leu-Leu is a small molecule with limited water solubility. Based on our own results, the solubility of Leu-Leu-Leu in water is ~2.5 mg/ml. Poor water solubility limits the therapeutic potential of this molecule.

In an effort to increase the solubility of Leu-Leu-Leu to enhance it's therapeutic potential, Leu-Leu-Leu was incorporated into lipid microparticles as follows:
j. 8 mg Leu-Leu-Leu was added to the tube and vortexed to combine. The mixture appeared white and opaque.
k. The Leu-Leu-Leu mixture was again placed over the ice-ethanol bath and fitted with the probe sonicator.
l. The mixture was sonicated on the same settings for 2.5 h, again replacing the ice-ethanol bath every 12-15 min.
m. After 2.5 h, the solution appeared transparent and when held up to light, appeared amber in color.
n. The solution was centrifuged again for 5 min at 12,000 rpm to remove any metal particulates.
o. The solution was then titrated to pH 7 with 1 M NaOH. The solution remained completely transparent and no crystallization occurred.

Leu-Leu-Leu was successfully prepared at 8 mg/ml and stabilized at pH 7 using the LMP formulation. The aqueous solubility of Leu-Leu-Leu at neutral pH was increased over three-fold using this new formulation. Even higher concentrations of Leu-Leu-Leu at neutral pH may be achieved using the lipid microparticle formulation. The LMP formulation greatly improves the therapeutic potential of Leu-Leu-Leu and other peptides/proteins with hydrophobic features.

The invention claimed is:

1. An aqueous colloidal lipid microparticle (LMP) pharmaceutical composition comprising water, a therapeutic compound in aqueous media at non-physiological pH, at least one lipid carrier, at least one emulsifying agent, and at least one excipient in an amount to allow titration of the pharmaceutical composition to, and maintain at, physiological pH, wherein the pharmaceutical composition is more soluble and less susceptible to precipitation in aqueous solution at physiological pH than the therapeutic compound, wherein said therapeutic compound comprises at least one hydrophobic GDF-5 related protein which is a naturally occurring or artificially created protein which comprises a cystine-knot-domain with an amino acid identity of at least 70% to the 102 aa cystine-knot-domain of human GDF-5 (amino acids 400-501 of SEQ ID NO:2), wherein the lipid carrier is an oil, and wherein the concentration of the lipid carrier ranges from 5-50 mg/ml.

2. The pharmaceutical composition according to claim 1, wherein the physiologically acceptable pH is within the range of 4 to 8.5.

3. The pharmaceutical composition according to claim 1, wherein the physiologically acceptable pH range is 5 to 7.5.

4. The pharmaceutical composition according to claim 1 wherein the lipid microparticles are lipid nanospheres.

5. The pharmaceutical composition according to claim 1, wherein the therapeutic compound further comprises at least one protein selected from the group consisting of growth factors, neurotrophins, hedgehog proteins, proteins of the TGF-family, antibodies, hormones, enzymes, membrane enzymes, lipoproteins and receptors.

6. The pharmaceutical composition according to claim 1, wherein the GDF-5 related protein is selected from the group consisting of human full-length GDF-5 (SEQ ID NO: 2), human full length GDF-5 lacking the signal peptide (amino acids 28 to 501 of SEQ ID NO: 2), human mature GDF-5 (SEQ ID NO:4 and amino acids 382 to 501 of SEQ ID NO: 1), human mature recombinant GDF-5 (amino acids 383 to 501 of SEQ ID NO: 2), a protein comprising the cystine-knot region of human GDF-5 (SEQ ID NO:7 and amino acids 400 to 501 of SEQ ID NO:2), human mature monomeric GDF-5 (SEQ ID NO: 3).

7. The pharmaceutical composition according to claim 1, wherein the therapeutic compound further comprises one or more substances selected from the group consisting of peptide-based drugs, oils, phospholipids, antioxidants, anti-inflammatory compounds, bioflavonoids, polyphenols, vitamins, glycolipids, porphyrins, antibiotics, antivirals, antidepressants, anxiolytics, antipsychotics, chemotherapeutic compounds, myricetin, estrogen, progesterone, testosterone, ceramide trihexosidase, neutral sphingomyelinase, and neutraceuticals.

8. The pharmaceutical composition according to claim 1, wherein the lipid carrier is a synthetic oil or a plant oil selected from the group consisting of olive oil, soybean oil, cottonseed oil, soybean oil, sesame oil, sunflower oil, safflower oil, avocado oil, peanut oil, walnut oil, almond oil and hazelnut oil.

9. The pharmaceutical composition according to claim 1, wherein the emulsifying agent is selected from the group consisting of phospholipids, distilled monoglycerides, diglycerides, acetic acid esters of monoglycerides, organic acid esters of monoglycerides, sorbitan esters of fatty acids, propylene glycol esters of fatty acids and polyglycerol esters of fatty esters.

10. The pharmaceutical composition according to claim 9, wherein the phospholipid is selected from the group consisting of phosphatidylserine, phosphatidylcholine and phosphatidyl-ethanolamine.

11. The pharmaceutical composition according to claim 1, wherein the at least one excipient allowing titration of the pharmaceutical composition to, and maintaining at, physiological pH comprises a) an acid or base substance in sufficient quantity to allow titration of the pharmaceutical composition to the desired physiological pH; and/or b) a buffer in sufficient quantity to allow titration of the pharmaceutical composition to the desired physiological pH and maintain the desired physiological pH.

12. The pharmaceutical composition according to claim 1, further comprising at least one antioxidant.

13. The pharmaceutical composition according to claim 12, wherein the antioxidant is selected from the group consisting of Vitamin E, Vitamin C, and bioflavonoid compounds.

14. The pharmaceutical composition according to claim 1, further comprising at least one odorant.

15. The pharmaceutical composition according to claim 14, wherein the odorant is selected from the group consisting of adenylate cyclase, guanylate cyclase, octyl isovalerate, cetralva, citronellol, amylcinnamaldehyde, CIS-jasmine, jasmal and musk 89.

16. An aqueous colloidal lipid microparticle (LMP) pharmaceutical composition comprising a therapeutic compound, a lipid carrier, and an emulsifying agent, wherein said therapeutic compound comprises at least one hydrophobic GDF-5 related protein which is a naturally occurring or artificially created protein which comprises a cystine-knot-domain with an amino acid identity of at least 70% to the 102 aa cystine-knot-domain of human GDF-5 (amino acids 400-501 of SEQ ID NO:2), wherein the lipid carrier is an oil, wherein the concentration of the lipid carrier ranges from 5-50 mg/ml and wherein said pharmaceutical composition comprises lipid microparticles with a size between 0.2 and 100 µm.

17. The pharmaceutical composition according to claim 16, further comprising at least one excipient in an amount to allow titration of the pharmaceutical composition to, and maintain at, physiological pH.

18. The pharmaceutical composition according to claim 17, wherein the at least one excipient allowing titration of the pharmaceutical composition to, and maintaining at, physiological pH comprises a) an acid or base substance in sufficient quantity to allow titration of the pharmaceutical composition to the desired physiological pH; and/or b) a buffer in sufficient quantity to allow titration of the pharmaceutical composition to the desired physiological pH and maintain the desired physiological pH.

19. The pharmaceutical composition according to claim 17, wherein the physiologically acceptable pH is within the range of 4 to 8.5.

20. The pharmaceutical composition according to claim 19, wherein the physiologically acceptable pH range is 5 to 7.5.

21. The pharmaceutical composition according to claim 16, wherein the lipid microparticles are lipid nanospheres.

22. The pharmaceutical composition according to claim 16, wherein the therapeutic compound further comprises at least one protein selected from the group consisting of growth factors, neurotrophins, hedgehog proteins, proteins of the TGF-family, antibodies, hormones, enzymes, membrane enzymes, lipoproteins and receptors.

23. The pharmaceutical composition according to claim 16, wherein the GDF-5 related protein is selected from the group consisting of human full-length GDF-5 (SEQ ID NO: 2), human full length GDF-5 lacking the signal peptide (amino acids 28 to 501 of SEQ ID NO: 2), human mature GDF-5 (SEQ ID NO:4 and amino acids 382 to 501 of SEQ ID NO: 1), human mature recombinant GDF-5 (amino acids 383 to 501 of SEQ ID NO: 2), a protein comprising the cystine-knot region of human GDF-5 (SEQ ID NO:7 and amino acids 400 to 501 of SEQ ID NO:2), human mature monomeric GDF-5 (SEQ ID NO: 3).

24. The pharmaceutical composition according to claim 16, wherein the therapeutic compound further comprises one or more substances selected from the group consisting of peptide-based drugs, oils, phospholipids, antioxidants, anti-inflammatory compounds, bioflavonoids, polyphenols, vitamins, glycolipids, porphyrins, antibiotics, antivirals, antidepressants, anxiolytics, antipsychotics, chemotherapeutic compounds, myricetin, estrogen, progesterone, testosterone, ceramide trihexosidase, neutral sphingomyelinase, and neutraceuticals.

25. The pharmaceutical composition according to claim 16, wherein the lipid carrier is a synthetic oil or a plant oil selected from the group consisting of olive oil, soybean oil, cottonseed oil, soybean oil, sesame oil, sunflower oil, safflower oil, avocado oil, peanut oil, walnut oil, almond oil and hazelnut oil.

26. The pharmaceutical composition according to claim 16, wherein the emulsifying agent is selected from the group consisting of phospholipids, distilled monoglycerides, diglycerides, acetic acid esters of monoglycerides, organic acid esters of monoglycerides, sorbitan esters of fatty acids, propylene glycol esters of fatty acids and polyglycerol esters of fatty esters.

27. The pharmaceutical composition according to claim 26, wherein the phospholipid is selected from the group consisting of phosphatidylserine, phosphatidylcholine and phosphatidyl-ethanolamine.

28. The pharmaceutical composition according to claim 16, further comprising at least one antioxidant.

29. The pharmaceutical composition according to claim 28, wherein the antioxidant is selected from the group consisting of Vitamin E, Vitamin C, and bioflavonoid compounds.

30. The pharmaceutical composition according to claim 16, further comprising at least one odorant.

31. The pharmaceutical composition according to claim 30, wherein the odorant is selected from the group consisting of adenylate cyclase, guanylate cyclase, octyl isovalerate, cetralva, citronellol, amylcinnamaldehyde, CIS-jasmine, jasmal and musk 89.

32. The pharmaceutical composition according to claim 16, wherein the concentration of the lipid carrier ranges from 16 to 30 mg/ml.

33. The pharmaceutical composition according to claim 16, wherein the concentration of the emulsifying agent ranges from 16 to 30 mg/ml.

34. An aqueous colloidal lipid microparticle (LMP) pharmaceutical composition comprising a therapeutic compound, a lipid carrier, and an emulsifying agent, wherein said therapeutic compound comprises at least one hydrophobic GDF-5 related protein which is a naturally occurring or artificially created protein which comprises a cystine-knot-domain with an amino acid identity of at least 70% to the 102 aa cystine-knot-domain of human GDF-5 (amino acids 400-501 of SEQ ID NO:2), wherein the lipid carrier is an oil, and wherein the concentration of the lipid carrier ranges from 16 to 30 mg/ml.

35. The pharmaceutical composition according to claim 34, further comprising at least one excipient in an amount to allow titration of the pharmaceutical composition to, and maintain at, physiological pH, wherein the pharmaceutical composition is more soluble and less susceptible to precipitation in aqueous solution at physiological pH than the therapeutic compound.

36. The pharmaceutical composition according to claim 35, wherein the at least one excipient allowing titration of the pharmaceutical composition to, and maintaining at, physiological pH comprises a) an acid or base substance in sufficient quantity to allow titration of the pharmaceutical composition to the desired physiological pH; and/or b) a buffer in sufficient quantity to allow titration of the pharmaceutical composition to the desired physiological pH and maintain the desired physiological pH.

37. The pharmaceutical composition according to claim 35, wherein the physiologically acceptable pH is within the range of 4 to 8.5.

38. The pharmaceutical composition according to claim 37, wherein the physiologically acceptable pH range is 5 to 7.5.

39. The pharmaceutical composition according to claim 34, wherein the pharmaceutical composition comprises lipid microparticles which are lipid nanospheres.

40. The pharmaceutical composition according to claim 34, wherein the therapeutic compound further comprises at least one protein selected from the group consisting of growth factors, neurotrophins, hedgehog proteins, proteins of the TGF-family, antibodies, hormones, enzymes, membrane enzymes, lipoproteins and receptors.

41. The pharmaceutical composition according to claim 34, wherein the GDF-5 related protein is selected from the group consisting of human full-length GDF-5 (SEQ ID NO: 2), human full length GDF-5 lacking the signal peptide (amino acids 28 to 501 of SEQ ID NO: 2), human mature GDF-5 (SEQ ID NO:4 and amino acids 382 to 501 of SEQ ID NO: 1), human mature recombinant GDF-5 (amino acids 383 to 501 of SEQ ID NO: 2), a protein comprising the cystine-knot region of human GDF-5 (SEQ ID NO:7 and amino acids 400 to 501 of SEQ ID NO:2), human mature monomeric GDF-5 (SEQ ID NO: 3).

42. The pharmaceutical composition according to claim 34, wherein the therapeutic compound further comprises one or more substances selected from the group consisting of peptide-based drugs, oils, phospholipids, antioxidants, anti-inflammatory compounds, bioflavonoids, polyphenols, vitamins, glycolipids, porphyrins, antibiotics, antivirals, antidepressants, anxiolytics, antipsychotics, chemotherapeutic compounds, myricetin, estrogen, progesterone, testosterone, ceramide trihexosidase, neutral sphingomyelinase, and neutraceuticals.

43. The pharmaceutical composition according to claim 34, wherein the lipid carrier is a synthetic oil or a plant oil selected from the group consisting of olive oil, soybean oil, cottonseed oil, soybean oil, sesame oil, sunflower oil, safflower oil, avocado oil, peanut oil, walnut oil, almond oil and hazelnut oil.

44. The pharmaceutical composition according to claim 34, wherein the emulsifying agent is selected from the group consisting of phospholipids, distilled monoglycerides, diglycerides, acetic acid esters of monoglycerides, organic acid esters of monoglycerides, sorbitan esters of fatty acids, propylene glycol esters of fatty acids and polyglycerol esters of fatty esters.

45. The pharmaceutical composition according to claim 44, wherein the phospholipid is selected from the group consisting of phosphatidylserine, phosphatidylcholine and phosphatidyl-ethanolamine.

46. The pharmaceutical composition according to claim 34, further comprising at least one antioxidant.

47. The pharmaceutical composition according to claim 46, wherein the antioxidant is selected from the group consisting of Vitamin E, Vitamin C, and bioflavonoid compounds.

48. The pharmaceutical composition according to claim 34, further comprising at least one odorant.

49. The pharmaceutical composition according to claim 48, wherein the odorant is selected from the group consisting of adenylate cyclase, guanylate cyclase, octyl isovalerate, cetralva, citronellol, amylcinnamaldehyde, CIS-jasmine, jasmal and musk 89.

50. The pharmaceutical composition according to claim 34, wherein the concentration of the emulsifying agent ranges from 16 to 30 mg/ml.

51. An aqueous colloidal lipid microparticle (LMP) pharmaceutical composition comprising a therapeutic compound, a lipid carrier, and an emulsifying agent, wherein said therapeutic compound comprises at least one hydrophobic GDF-5 related protein which is a naturally occurring or artificially created protein which comprises a cystine-knot-domain with an amino acid identity of at least 70% to the 102 aa cystine-knot-domain of human GDF-5 (amino acids 400-501 of SEQ ID NO:2), wherein the lipid carrier is an oil, wherein the concentration of the lipid carrier ranges from 5-50 mg/ml and, wherein the concentration of the emulsifying agent ranges from 16 to 30 mg/ml.

52. The pharmaceutical composition according to claim 51, further comprising at least one excipient in an amount to allow titration of the pharmaceutical composition to, and maintain at, physiological pH.

53. The pharmaceutical composition according to claim 52, wherein the at least one excipient allowing titration of the pharmaceutical composition to, and maintaining at, physiological pH comprises a) an acid or base substance in sufficient quantity to allow titration of the pharmaceutical composition to the desired physiological pH; and/or b) a buffer in sufficient quantity to allow titration of the pharmaceutical composition to the desired physiological pH and maintain the desired physiological pH.

54. The pharmaceutical composition according to claim 52, wherein the physiologically acceptable pH is within the range of 4 to 8.5.

55. The pharmaceutical composition according to claim 54, wherein the physiologically acceptable pH range is 5 to 7.5.

56. The pharmaceutical composition according to claim 51, wherein the pharmaceutical composition comprises lipid microparticles which are lipid nanospheres.

57. The pharmaceutical composition according to claim 51, wherein the therapeutic compound further comprises at least one protein selected from the group consisting of growth factors, neurotrophins, hedgehog proteins, proteins of the TGF-family, antibodies, hormones, enzymes, membrane enzymes, lipoproteins and receptors.

58. The pharmaceutical composition according to claim 51, wherein the GDF-5 related protein is selected from the group consisting of human full-length GDF-5 (SEQ ID NO: 2), human full length GDF-5 lacking the signal peptide (amino acids 28 to 501 of SEQ ID NO: 2), human mature GDF-5 (SEQ ID NO:4 and amino acids 382 to 501 of SEQ ID NO: 1), human mature recombinant GDF-5 (amino acids 383 to 501 of SEQ ID NO: 2), a protein comprising the cystine-knot region of human GDF-5 (SEQ ID NO:7 and amino acids 400 to 501 of SEQ ID NO:2), human mature monomeric GDF-5 (SEQ ID NO: 3).

59. The pharmaceutical composition according to claim 51, wherein the therapeutic compound further comprises one or more substances selected from the group consisting of peptide-based drugs, oils, phospholipids, antioxidants, anti-inflammatory compounds, bioflavonoids, polyphenols, vitamins, glycolipids, porphyrins, antibiotics, antivirals, antidepressants, anxiolytics, antipsychotics, chemotherapeutic compounds, myricetin, estrogen, progesterone, testosterone, ceramide trihexosidase, neutral sphingomyelinase, and neutraceuticals.

60. The pharmaceutical composition according to claim 51, wherein the lipid carrier is a synthetic oil or a plant oil selected from the group consisting of olive oil, soybean oil, cottonseed oil, soybean oil, sesame oil, sunflower oil, safflower oil, avocado oil, peanut oil, walnut oil, almond oil and hazelnut oil.

61. The pharmaceutical composition according to claim 51, wherein the emulsifying agent is selected from the group consisting of phospholipids, distilled monoglycerides, diglycerides, acetic acid esters of monoglycerides, organic acid esters of monoglycerides, sorbitan esters of fatty acids, propylene glycol esters of fatty acids and polyglycerol esters of fatty esters.

62. The pharmaceutical composition according to claim 61, wherein the phospholipid is selected from the group consisting of phosphatidylserine, phosphatidylcholine and phosphatidyl-ethanolamine.

63. The pharmaceutical composition according to claim 51, further comprising at least one antioxidant.

64. The pharmaceutical composition according to claim 63, wherein the antioxidant is selected from the group consisting of Vitamin E, Vitamin C, and bioflavonoid compounds.

65. The pharmaceutical composition according to claim 51, further comprising at least one odorant.

66. The pharmaceutical composition according to claim 65, wherein the odorant is selected from the group consisting of adenylate cyclase, guanylate cyclase, octyl isovalerate, cetralva, citronellol, amylcinnamaldehyde, CIS-jasmine, jasmal and musk 89.

* * * * *